US005665892A

United States Patent [19]
Van Assche et al.

[11] Patent Number: 5,665,892
[45] Date of Patent: Sep. 9, 1997

[54] SUCROSE PHOSPHATE SYNTHASE (SPS), ITS PROCESS FOR PREPARATION ITS CDNA, AND UTILIZATION OF CDNA TO MODIFY THE EXPRESSION OF SPS IN PLANT CELLS

[75] Inventors: Charles Van Assche, Marseille; Danielle Lando; Jean Michel Bruneau, both of Paris, all of France; Toni Alois Voelker, Davis, Calif.; Monica Gervais, Saint-Leu-La-Foret, France

[73] Assignee: Calgene, Inc., Davis, Calif.

[21] Appl. No.: 175,471

[22] Filed: Dec. 27, 1993

Related U.S. Application Data

[63] Continuation of Ser. No. 672,646, Mar. 18, 1991, abandoned.

[30] Foreign Application Priority Data

Jul. 20, 1990 [EP] European Pat. Off. .............. 90402084

[51] Int. Cl.$^6$ .............................. A01H 4/00; C12N 15/82; C12N 5/14
[52] U.S. Cl. .................... 800/205; 536/23.2; 435/320.1; 435/172.3; 435/411; 435/423; 800/DIG. 44
[58] Field of Search .................. 536/23.6, 23.2; 435/320.1, 172.3, 240.4; 800/205, DIG. 44; 672/646

[56] References Cited

PUBLICATIONS

Boswell et al. in Computational Molecular Biology Sources and Methods for Sequence Analysis (Lesk, ed.) Oxford University Press, Oxford, 1988, pp. 170–171.
W. Kalt–Torres, et al., "Isolation and characterization of multiple forms of maize leaf sucrose–phosphate synthase," *Physiol. Plantarum* (1987) 70:653–658.
Kerr, et al., "Resolution of two molecular forms of sucrose–phosphate synthase from maize, soybean and spinach leaves," *Planta* (1987) 170:515–519.
Su, et al., "Purification and Properties of Sucrose Synthase from Maize Kernels," *Plant Physiology* (1978) 61(3):389–393.
Bruneau, et al., "Sucrose Phosphate Synthase, a Key Enzyme for Sucrose Biosynthesis in Plants," *Plant Physiol.* (1991) 43–478.
American Heritage Dictionary, second college edition, Houghton Miflin Co., Boston, 1982, p. 1340.
Kalt–Torres, et al. (1987) Physiol Plantarum 70:653–658.
Lee et al. (1988) Science 239:1288–1291.
Dickinson, et al. (Feb. 1991) Plant Physiol. 95:420–425.
von Schaewen, et al. (1990) The Embo Journal 9(10):3033–3044.
Sonnewald, et al. (1993) Planta 189:174–181.
Werr, et al. (1985) EMBO J. 4:1373–1380.

*Primary Examiner*—Che S. Chereskin
*Attorney, Agent, or Firm*—Rae-Venter Law Group, P.C.

[57] ABSTRACT

Sucrose phosphate synthase (SPS), its process for preparation, its cDNA, and utilization of cDNA to modify the expression of SPS in the plant cells are provided.

67 Claims, 20 Drawing Sheets

FIG. 3

SPS 90 peptides

A8  ThrTrpIleLys

B4  TyrValValGluLeuAlaArg

B11 SerMetProProIleTrpAlaGluValMetArg

SPS 30 kd peptides

4K  LeuArgProAspGlnAspTyrLeuMetHisIleSerHisArg

12N TrpSerHisAspGlyAlaArg

```
                              TGATCTGGTCGTAA
                               G  C  C TC G
```

4K2
```
GATGACTAATATGCAT
 TG  G  G
  T
```

4K4
```
                                        B11A  CGCATTACCTCTCGCCCA
                                               C  T C   T
```

```
           >
GACCAAGAGTACCTATGCA----->
        C  T T  G T
         T  G   T
```

4K3
```
              TGCATTAGATAATCCTGATC----->
               C  G G  T
                 G    G
```

4K
LeuArgProAspGlnAsnAspTyrLeuMetHisIleSerHisArg
TTAAGACCAGACCAAGAGACTACTTAATGCACATAAGACACAGA
 C  CGC  C   T   G T TC C  T   CTCC TC  C
 T   G   C   T     T G  G  C          T G  G
                     T      T              T

TCTGCCAAATTGGGTGGGCAT----->B11
                                          C         G   C
                                          T         C
```

B11
SerMetProProIleTrpAlaGluValMetArg
TCAATGCCACCAATATGGGCAGAAGTAATGCGA
AGC  C  C   C  C G C  G  AC    G
 G   G  G   G  T T    G         T
 T   T  T      T T    T

11C
```
ATGCCTCCTATATGGGCTGA----->
  C  C C   C  C
     T     T
```

FIG.7A

```
EcoRI
GAATTCCGGC GTGGGCGCTG GGCTAGTGCT CCCGCAGCGA GCGATCTGAG AGAACGGTAG   60
2
                                                     BamHI
AGTTCCGGCC GGGCGCGCGG GAGAGGAGGA GGGTCGGGGCG GGGAGGATCC G ATG GCC  117
                                                          MET Ala
                                                          106
                          KpnI
GGG AAC GAG TGG ATC AAT GGG TAC CTG GAG GCG ATC CTC GAC AGC CAC   165
Gly Asn Glu Trp Ile Asn Gly Tyr Leu Glu Ala Ile Leu Asp Ser His
                                 142

ACC TCG TCG CGG GGT GCC GGC GGC GGC GGC GGG GAC CCC AGG           213
Thr Ser Ser Arg Gly Ala Gly Gly Gly Gly Gly Asp Pro Arg

TCG CCG ACG AAG GCG AGC CCC CGC GCG CAC ATG AAC TTC AAC           261
Ser Pro Thr Lys Ala Ser Pro Arg Ala His Met Asn Phe Asn
                                                    SalI
CCC TCG CAC TAC TTC GTC GAG GAG GTG GTC AAG GGC GTC GAC GAG AGC   309
Pro Ser His Tyr Phe Val Glu Glu Val Val Lys Gly Val Asp Glu Ser
                                                         299

GAC CTC CAC CGG ACG TGG ATC AAG GTC GTC GCC ACC CGC AAC GCC CGC   357
Asp Leu His Arg Thr Trp Ile Lys Val Val Ala Thr Arg Asn Ala Arg
                        AB
```

FIG.7B

```
                                      XhoI
                                      ┌─┐
GAG CGC AGC ACC AGG CTC GAG AAC ATG TGC TGG CGG ATC TGG CAC CTC    405
Glu Arg Ser Thr Arg Leu Glu Asn Met Cys Trp Arg Ile Trp His Leu
                        374

GCG CGC AAG AAG CAG CTG GAG GGC ATC CAG AGA ATC TCG                453
Ala Arg Lys Lys Gln Leu Glu Gly Ile Gln Arg Ile Ser

GCA AGA AGG AAG GAA CAG GAG CGT CGT GAG GCG ACG GAG GAC            501
Ala Arg Arg Lys Glu Gln Glu Val Arg Arg Glu Ala Thr Glu Asp

CTG GCC GAG GAT CTG TCA GAA GGC GAG AAG GAC ACC ATC GGC GAG        549
Leu Ala Glu Asp Leu Ser Glu Gly Glu Lys Asp Thr Ile Gly Glu

CTT GCG CCG GTT GAG ACC AAG AAG AAG TTC CAG AGG AAC TTC TCT        597
Leu Ala Pro Val Glu Thr Lys Lys Lys Phe Gln Arg Asn Phe Ser

HindIII
                                           ┌─┐
GAC CTT ACC GTC TGG TCT GAC GAC AAT AAG GAG AAG CTT TAC ATT        645
Asp Leu Thr Val Trp Ser Asp Asp Asn Lys Glu Lys Leu Tyr Ile
                                               635

GTG CTC ATC AGC GTG CAT GGT CTT GTT CGT GGA GAA AAC ATG GAA CTA    693
Val Leu Ile Ser Val His Gly Leu Val Arg Gly Glu Asn Met Glu Leu
```

FIG.7C

```
GGT CGT GAT TCT GAT ACA GGT GGC CAG GTG AAA TAT GTG GTC GAA CTT    741
Gly Arg Asp Ser Asp Thr Gly Gly Gln Val Lys Tyr Val Val Glu Leu
                                                      B4

GCA AGA GCG ATG TCA ATG ATG CCT GGA GTG TAC AGG GTG GAC CTC TTC    789
Ala Arg Ala Met Ser Met Met Pro Gly Val Tyr Arg Val Asp Leu Phe

ACT CGT CAA GTG TCA TCT CCT GAC GTG GAC TGG AGC TAC GGT GAG CCA    837
Thr Arg Gln Val Ser Ser Pro Asp Val Asp Trp Ser Tyr Gly Glu Pro

ACC GAG ATG TTA TGC GCC GGT TCC AAT GAT GGA GAG GGG ATG GGT GAG    885
Thr Glu Met Leu Cys Ala Gly Ser Asn Asp Gly Glu Gly Met Gly Glu

AGT GGC GGA GCC TAC ATT GTG CGC ATA CCG TGT GGG CCG CGG GAT AAA    933
Ser Gly Gly Ala Tyr Ile Val Arg Ile Pro Cys Gly Pro Arg Asp Lys

TAC CTC AAG AAG GAA GCG TTG TGG CCT TAC CTC CAA GAG TTT GTC GAT    981
Tyr Leu Lys Lys Glu Ala Leu Trp Pro Tyr Leu Gln Glu Phe Val Asp

GGA GCC CTT GCG CAT ATC CTG AAC ATG TCC AAG GCT CTG GGA GAG CAG   1029
Gly Ala Leu Ala His Ile Leu Asn Met Ser Lys Ala Leu Gly Glu Gln

GTT GGA AAT GGG AGG CCA GTA CTG CCT TAC CTG CCC TAC GTG ATA CAT GGG CAC TAT   1077
Val Gly Asn Gly Arg Pro Val Leu Pro Tyr Val Ile His Gly His Tyr

GCC GAT GCT GGA GAT GTT GCT CTC CTT TCT GGT GCG CTG AAT GTG   1125
Ala Asp Ala Gly Asp Val Ala Leu Leu Ser Gly Ala Leu Asn Val
```

FIG. 7D

```
CCA ATG GTC CTC ACT GGC CAC TCA CTT GGG AGG AAC AAG CTG GAA CAA   1173
Pro Met Val Leu Thr Gly His Ser Leu Gly Arg Asn Lys Leu Glu Gln

CTG CTG AAG CAA GGG CGC ATG TCC AAG GAG GAG ATC GAT TCG ACA TAC   1221
Leu Leu Lys Gln Gly Arg Met Ser Lys Glu Glu Ile Asp Ser Thr Tyr

AAG ATC ATG AGG CGT ATC GAG GGT GAG GAG CTG GCC CTG GAT GCG TCA   1269
Lys Ile Met Arg Arg Ile Glu Gly Glu Glu Leu Ala Leu Asp Ala Ser

GAG CTT GTA ATC ACG AGC ACA AGG CAG GAG ATT GAT CAG TGG GGA       1317
Glu Leu Val Ile Thr Ser Thr Arg Gln Glu Ile Asp Gln Trp Gly
                                                HindIII
                                                ———
TTG TAC GAT GGA TTT GAT GTC AAG CTT GAG AAA GTG CTG AGG GCA CGG   1365
Leu Tyr Asp Gly Phe Asp Val Lys Leu Glu Lys Val Leu Arg Ala Arg
                                 1340
                                                NcoI
                                                ———
GCG AGG CGC GGG GTT AGC TGC CAT GGT CGT TAC ATG CCT AGG ATG GTG   1413
Ala Arg Arg Gly Val Ser Cys His Gly Arg Tyr Met Pro Arg Met Val
                                     1387

GTG ATT CCT CCG GGA ATG GAT TTC AGC AAT GTT GTA GTT CAT GAA GAC   1461
Val Ile Pro Pro Gly Met Asp Phe Ser Asn Val Val His Glu Asp
```

FIG.7E

```
ATT GAT GGG GAT GGT GAC GTC AAA GAT GAT ATC GTT GGT TTG GAG GGT   1509
Ile Asp Gly Asp Gly Asp Val Lys Asp Asp Ile Val Gly Leu Glu Gly

GCC TCA ATG CCC AAG TCA ATG CCC CCA ATT TGG GCC GAA GTG ATG CGG TTC   1557
Ala Ser Pro Lys Ser Met Pro Pro Ile Trp Ala Glu Val Met Arg Phe
                            B11

CTG ACC AAC CCT CAC AAG CCG ATG ATC CTG GCG TTA TCA AGA CCA GAC   1605
Leu Thr Asn Pro His Lys Pro Met Ile Leu Ala Leu Ser Arg Pro Asp

CCG AAG AAC ATC ACT ACC CTC GTC AAA GCC TTT GGA GAG TGT CGT   1653
Pro Lys Asn Ile Thr Thr Leu Val Lys Ala Phe Gly Glu Cys Arg

CCA CTC AGG GAA CTT GCA AAC CTT ACT CTG ATC ATG GGT AAC AGA GAT   1701
Pro Leu Arg Glu Leu Ala Asn Leu Thr Leu Ile Met Gly Asn Arg Asp

GAC ATC GAC GAC ATG TCT GCT GGC AAT GCC AGT GTC CTC ACC ACA GTT   1749
Asp Ile Asp Asp Met Ser Ala Gly Asn Ala Ser Val Leu Thr Thr Val

CTG AAG GAT TAT GAT CTG TAC GGA AGC GTG GCG TTC CCT   1797
Leu Lys Asp Tyr Asp Leu Tyr Gly Ser Val Ala Phe Pro
                              BglII
                               |
AAG CAT CAC AAT CAG GCT GAC GTC CCG GAG ATC TAT CGC CTC GCG GCC   1845
Lys His His Asn Gln Ala Asp Val Pro Glu Ile Tyr Arg Leu Ala Ala
                                        1827
```

FIG. 7F

```
AAA ATG AAG GGC GTC TTC ATC AAC CCT GCT CTC GTT GAG CCG TTT GGT    1893
Lys Met Lys Gly Val Phe Ile Asn Pro Ala Leu Val Glu Pro Phe Gly

CTC ACC CTG ATC GAG GCT GCG GCA CAC GGA CTC CCG ATA GTC GCT ACC    1941
Leu Thr Leu Ile Glu Ala Ala Ala His Gly Leu Pro Ile Val Ala Thr

SalI
                        |—|
AAG AAT GGT GGT CCG GTC GAC ATT ACA AAT GCA TTA AAC AAC GGA CTG    1989
Lys Asn Gly Gly Pro Val Asp Ile Thr Asn Ala Leu Asn Asn Gly Leu
                    1958
                                                        HindIII
                                                        |—|
CTC GTT GAC CCA CAC GAC AAG AAC GCC ATC GCT GAT GCA CTG CTG AAG    2037
Leu Val Asp Pro His Asp Lys Asn Ala Ile Ala Asp Ala Leu Leu Lys
                                                            2036

CTT GTG GCA GAC AAG AAC CTG TGG CAG GAA TGC CGG AGA AAC GGG CTG    2085
Leu Val Ala Asp Lys Asn Leu Trp Gln Glu Cys Arg Arg Asn Gly Leu

CGC AAC ATC CAC CTC TAC TCA TGG CCG GAG CAC TGC CGC ACT TAC CTC    2133
Arg Asn Ile His Leu Tyr Ser Trp Pro Glu His Cys Arg Thr Tyr Leu

ACC AGG GTG GCC GGG TGC CGG TTA AGG AAC CCG AGG TGG CTG AAG GAC    2181
Thr Arg Val Ala Gly Cys Arg Leu Arg Asn Pro Arg Trp Leu Lys Asp
```

FIG. 7G

```
ACA CCA GCA GAT GCC GGA GCC GAT GAG GAG TTC CTG GAG GAT TCC   2229
Thr Pro Ala Asp Ala Gly Ala Asp Glu Glu Phe Leu Glu Asp Ser
                                                           NcoI
                                                           2229

ATG GAC GCT CAG GAC CTG TCA CTC CGT CTG TCC ATC GAC GAG AAG   2277
Met Asp Ala Gln Asp Leu Ser Leu Arg Leu Ser Ile Asp Glu Lys

AGC TCG CTG AAC ACT AAC GAT CCA CTG TGG TTC GAC CCC CAG GAT CAA   2325
Ser Ser Leu Asn Thr Asn Asp Pro Leu Trp Phe Asp Pro Gln Asp Gln

GTG CAG AAG ATC ATG AAC AAC ATC AAG CAG TCA GCG CTT CCT CCG   2373
Val Gln Lys Ile Met Asn Asn Ile Lys Gln Ser Ala Leu Pro Pro

TCC ATG TCC TCA GTC GCA GCC GAG GGC ACA AGC ACC ATG AAC AAA   2421
Ser Met Ser Ser Val Ala Ala Glu Gly Thr Ser Thr Met Asn Lys

TAC CCA CTC CTG CGC CGG CGC TTG TTC GTC ATA GCT GTG GAC       2469
Tyr Pro Leu Leu Arg Arg Arg Leu Phe Val Ile Ala Val Asp
                                                         PstI
                                                         2511

TGC TAC CAG GAC GAT GGC CGT GCT AGC AAG AAG ATG CTG CAG GTG ATC   2517
Cys Tyr Gln Asp Asp Gly Arg Ala Ser Lys Lys Met Leu Gln Val Ile
```

FIG. 7H

```
                                                              BglII
                                                              |
CAG GAA GTT TTC AGA GCA GTC CGA TCG GAC TCC CAG ATG TTC AAG ATC    2565
Gln Glu Val Phe Arg Ala Val Arg Ser Asp Ser Gln Met Phe Lys Ile
                                                              2562
              SalI
              |
TCA GGG TTC ACG CTG TCG ACT GCC ATG CCG TTG TCC GAG ACA CTC CAG    2613
Ser Gly Phe Thr Leu Ser Thr Ala Met Pro Leu Ser Glu Thr Leu Gln
                  2581
      PstI
      |
CTT CTG CAG CTC GGC AAG ATC CCA GCG ACC GAC TTC GAC GCC CTC ATC    2661
Leu Leu Gln Leu Gly Lys Ile Pro Ala Thr Asp Phe Asp Ala Leu Ile
          2622

TGT GGC AGC GGC AGC GAG GTG TAC TAT CCT GGC ACG GCG AAC TGC ATG    2709
Cys Gly Ser Gly Ser Glu Val Tyr Tyr Pro Gly Thr Ala Asn Cys Met

GAC GCT GAA GGA AAG CTG CGC CCA GAT CAG GAC TAT CTG ATG CAC ATC    2757
Asp Ala Glu Gly Lys Leu Arg Pro Asp Gln Asp Tyr Leu Met His Ile
                                        ----------------------
                                                 4K
AGC CAC CGC TGG TCC CAT GAC GGC GCG AGG CAG ACC ATA GCG AAG CTC    2805
Ser His Arg Trp Ser His Asp Gly Ala Arg Gln Thr Ile Ala Lys Leu
-----------------------------------------------------------
                          12M
```

FIG. 7I

```
ATG GGC GCT CAG GAC GGT TCA GGC GAC GCT GTC GAG CAG GAC GTG GCG   2853
Met Gly Ala Gln Asp Gly Ser Gly Asp Ala Val Glu Gln Asp Val Ala

TCC AGT AAT GCA CAC TGT GTC GCG TTC CTC ATC AAA GAC CCC CAA AAG   2901
Ser Ser Asn Ala His Cys Val Ala Phe Leu Ile Lys Asp Pro Gln Lys

GTG AAA ACG GTC GAT GAG ATG AGG GAG CGG CTG AGG ATG CGT GGT CTC   2949
Val Lys Thr Val Asp Glu Met Arg Glu Arg Leu Arg Met Arg Gly Leu
                                          PstI
                                           |
CGC TGC CAC ATC ATG TAC TGC AGG AAC TCG ACA AGG CTT CAG GTT GTC   2997
Arg Cys His Ile Met Tyr Cys Arg Asn Ser Thr Arg Leu Gln Val Val
                            2972

CCT CTG CTA GCA TCA CAG GCA CTC AGG TAT CTT TCC GTG CGC            3045
Pro Leu Leu Ala Ser Gln Ala Leu Arg Tyr Leu Ser Val Arg

TGG GGC GTA TCT GTG GGG AAC ATG TAT CTG ATC ACC GGG GAA CAT GGC   3093
Trp Gly Val Ser Val Gly Asn Met Tyr Leu Ile Thr Gly Glu His Gly
            XbaI
             |
GAC ACC GAT CTA GAG GAG ATG CTA TCC GGG CTA CAC AAG ACC GTG ATC   3141
Asp Thr Asp Leu Glu Glu Met Leu Ser Gly Leu His Lys Thr Val Ile
        3103
```

FIG.7J

| | |
|---|---|
| GTC CGT GGC GTC ACC GAG AAG GGT TCG GAA GCA CTG GTG AGG AGC CCA<br>Val Arg Gly Val Thr Glu Lys Gly Ser Glu Ala Leu Val Arg Ser Pro | 3189 |
| GGA AGC TAC AAG AGG GAC GAT GTC GTC CCG TCT GAG ACC CCC TTG GCT<br>Gly Ser Tyr Lys Arg Asp Asp Val Val Pro Ser Glu Thr Pro Leu Ala | 3237 |
| GCG TAC ACG ACT GGT GAG CTG AAG CTG AAG GCC GAC GAG ATC ATG CGG GCT CTG<br>Ala Tyr Thr Thr Gly Glu Leu Lys Lys Ala Asp Glu Ile Met Arg Ala Leu | 3285 |
| AAG CAA GTC TCC AAG ACT TCC AGC GGC ATG TGAATTTGAT GCTTCTTTTA<br>Lys Gln Val Ser Lys Thr Ser Ser Gly Met | 3335 |
| CATTTGTCCTTTCTTCACTGCTATATAAAATAAGTTGTGAACAGTACCGCGGGTGTGT | 3395 |
| ATATATATATATTGCAGTGACAAATAAAAACAGGACACTGCTAACTATACTGGTGAATATACG | 3455 |
| ACTGTCAAGATTGTATGCTAAGTACTCCATTTCTCAATGTATCAATCGGAATTC<br>                                                           EcoRI<br>                                                           3505 | 3509 |

SUCROSE PHOSPHATE SYNTHASE (SPS), ITS PROCESS FOR PREPARATION ITS CDNA, AND UTILIZATION OF CDNA TO MODIFY THE EXPRESSION OF SPS IN PLANT CELLS

This is a continuation of application Ser. No. 07/672,646, filed Mar. 18, 1991 now abandoned.

The present invention relates to the sucrose phosphate synthase (SPS), its process for preparation, its cDNA, and utilization of cDNA to modify the expression of SPS in the plant cells.

Difficulties in the purification of sucrose phosphate synthase (SPS) from plants have interferred with efforts to characterize this enzyme. SPS catalyses the formation of sucrose phosphate, the sucrose precursor molecule, from fructose-6 phosphate and UDP-glucose in photosynthetically active plant cells. Sucrose phosphatase then acts on the sucrose phosphate moiety, in an irreversible reaction, to remove the phosphate and to release sucrose ready to translocate from the mature leaf (source) to any tissue requiring photoassimilate (sink), especially growing tissues including young leaves, seeds, and roots.

Because SPS is considered a rate limiting enzyme in the pathway providing sucrose to growing tissue, the study of SPS and its activity is of special interest. In a recent publication, Walker, J. L. & Huber, S. C., *Plant Phys.* (1989) 89 : 518–524, the purification and preliminary characterization of spinach (*Spinachia oleracea*) SPS was reported. However, monoclonal antibodies specific to the spinach SPS were found to be non-reactive with all other plants tested, "closely related" and "relatively unrelated species", including corn (*Zea maize*), soybean (*Glycine max*), barley (*Hordeum vulgare*), and sugar beet (*Beta vulgaris*). Thus, additional purified sources of SPS enzyme are needed for effective characterization of this factor. Especially of interest is the characterization of the corn SPS because of its very high export rates, as compared for example, to SPS levels of activity as found in the leaves of soybean.

With the advent of biotechnology, the ability to modify various properties of plants, especially agronomically important crops, is of interest. In this regard, it would be useful to determine the coding sequence for an SPS gene to probe other crop sources, to use such coding sequences to prepare DNA expression constructs capable of directing the expression of the SPS gene in a plant cell and to express a DNA sequence encoding an SPS enzyme in a plant to measure the effects on crop yield due to the increased rate of sucrose translocation to growing tissues.

DETAILED DESCRIPTION OF THE FIGURES

FIG. 3 shows peptide sequences (SEQ ID NOS: 1–5) derived from the SPS protein: peptides A8 (SEQ ID NO: 1), B4 (SEQ ID NO: 2) and B11 (SEQ ID NO: 3) correspond to the SPS 90 kilodalton (kd) protein; peptides 4K (SEQ ID NO: 4) and 12N (SEQ ID NO: 5) correspond to the SPS 30 kd protein. All peptides are typed N→C terminal.

FIG. 4 shows the oligonucleotides used for the PCR reactions CD3 (11C (SEQ ID NO: 9) and 4K3 (SEQ ID NO: 10)) and CD4 (11B (SEQ ID NO: 11) and 4K1S (SEQ ID NO: 12)) in relation to the B11 (SEQ ID NO: 3) and 4K (SEQ ID NO: 4) peptides (antisense sequences are presented upside down). Arrows point to the direction the oligonucleotides will prime the polymerase.

Figure 5A:
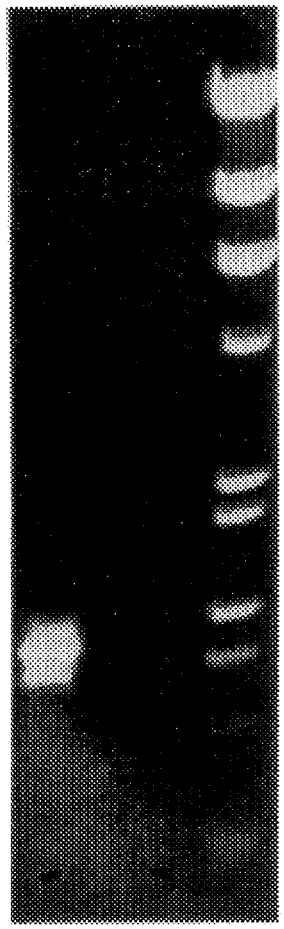
Figure 5B:
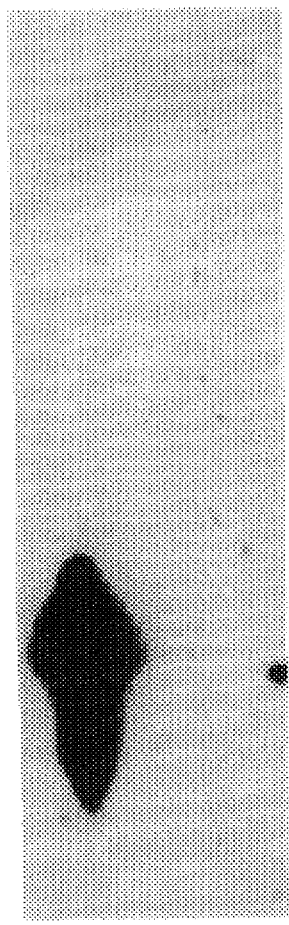

FIG. 5A shows the results of an agarose gel electrophoresis of CD3 and CD4 PCR reactions. The sizes are given in kb, where M=molecular size marker in kilobase pairs (kb). FIG. 5B shows an autoradiograph of Southern blot of CD3 and CD4 PCR reactions probed with oligonucleotide 4K5 (SEQ ID NO: 13), where M=molecular size marker in kb.

Figure 6:
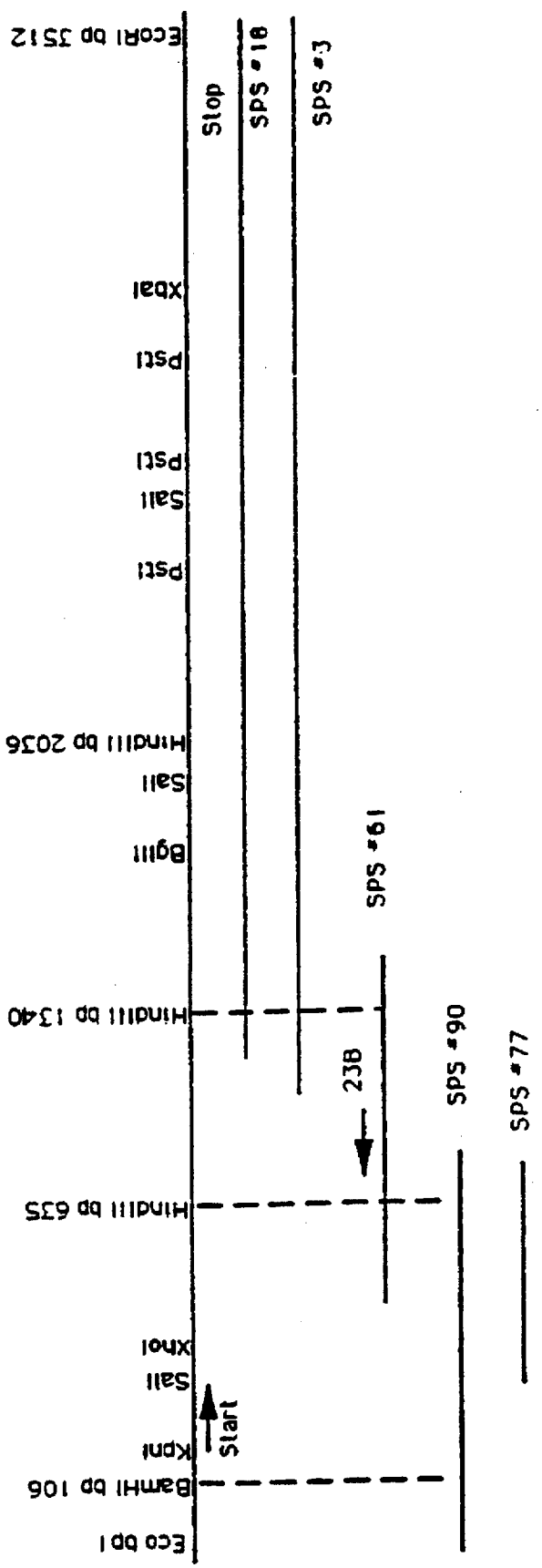

FIG. 6 shows schematic diagrams representing SPS cDNA and selected clones SPS#3, SPS#18, SPS#61, SPS#77 and SPS#90. The upper bar represents the entire 3509 bp combined map and selected restriction sites. The translation stop and start codons are indicated.

FIG. 7 shows the assembled SPS cDNA sequence and selected restriction sites. The sequences of clones SPS#90, SPS#61 and SPS#3 were fused at the points indicated in FIG. 6. The SPS reading frame is translated. All SPS protein derived peptide sequences are indicated.

Figure 8:
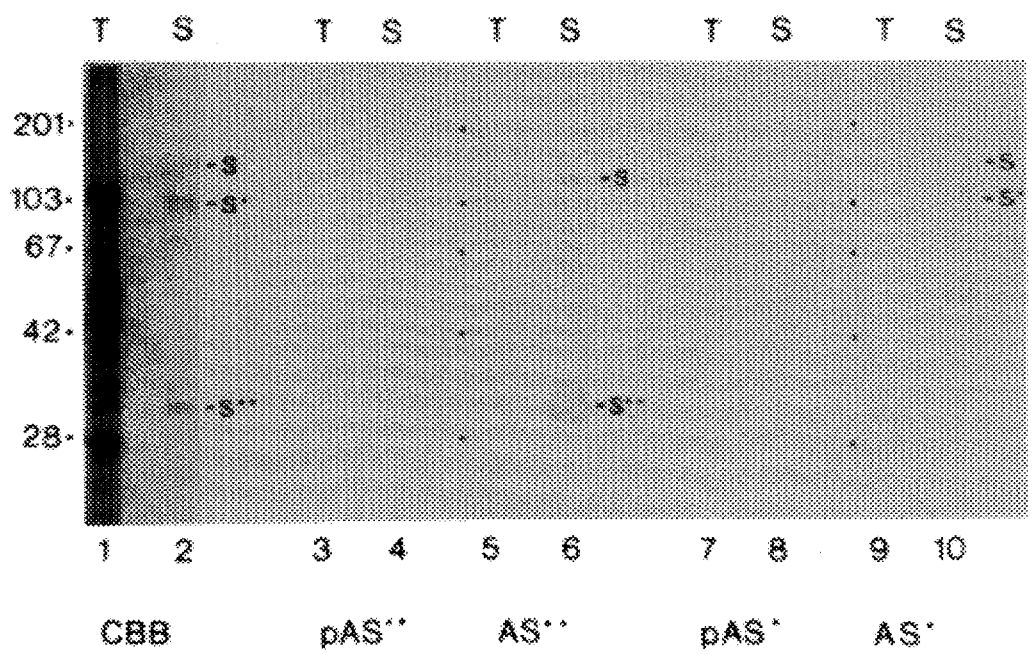

FIG. 8 shows Western blots showing characteristics of rabbit SPS 90 and SPS 30 antisera. Lanes T=total protein extract from corn leaf; Lanes S=immunopurified SPS; Panel CBB=Coomassie Blue-stained protein; pAS=preimmune serum, SPS 30 rabbit; AS=immune serum anti SPS 30; pAS*=preimmune serum, SPS 90 rabbit; AS*=immune serum anti SPS 90. Molecular weight markers at left, where indicated; S=SPS 120 kilodalton (kd) polypeptide; S*=SPS 90 kd polypeptide; S**=SPS 30 kd polypeptide.

Figure 9A:
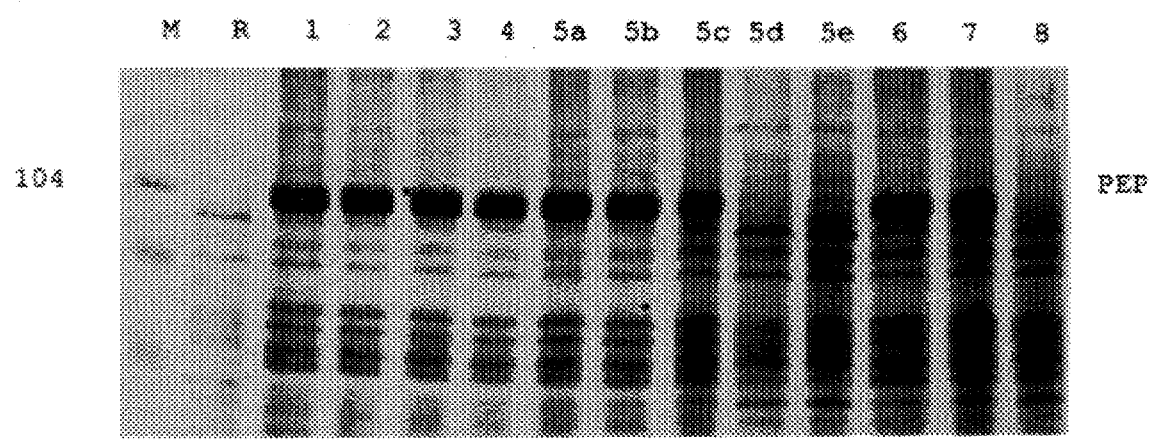

FIG. 9A shows a Coomassie Blue-stained gel of total protein isolated from a 30 day old corn plant. M=size marker in kilodaltons (kd); R=roots; 1–8=leaf numbers counting from the bottom of the plant. Leaf 5 has been cut into 5 segments from the leaf tip (5a) to the end of the sheath (5e). PEP=phosphoenolpyruvate carboxylase.

Figure 9B:
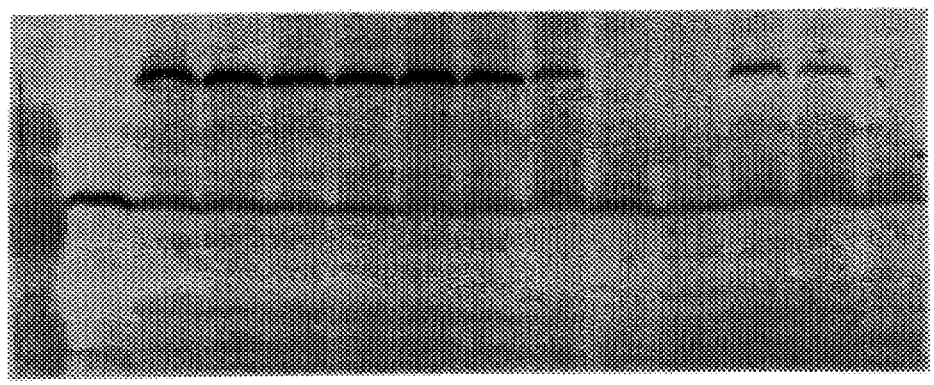

FIG. 9B shows the results of Western blot analysis of a replicate of the gel shown in FIG. 9A using a mixture of anti SPS 30 and anti SPS 90 antisera against total plant protein isolated from a 30 day old corn plant. The signal corresponding to SPS appears at 120–140 kd.

In a first embodiment, proteins having the sucrose phosphate synthase (SPS) activity, namely, a protein capable of catalyzing the formation of sucrose phosphate from fructose-6-phosphate and UDP-glucose substrates, are provided. Among the preferred proteins of this invention are such proteins obtainable from corn which are substantially free of other proteins.

By "protein" is meant any amino acid sequence, including a protein, polypeptide, or peptide fragment, whether obtained from plant or synthetic sources, which demonstrates the ability to catalyze the formation of sucrose phosphate. An SPS of this invention will include sequences which are modified, such as sequence which have been mutated, truncated, increased, contain codon substitutions as a result of the degeneracy of the DNA code, and the like as well as sequences which are partially or wholly artificially synthesized, so long as the synthetic sequence retains the characteristic SPS activity.

By "substantially free from other proteins" is meant that the protein has been partially purified away from proteins found in the plant cell. Such a protein of this invention will demonstrate a specific enzymatic activity of at least greater than 0.05, more preferably at least greater than at least 0,30, wherein specific enzymatic activity (sA) is measured in units which correspond to 1 μm (micromole) of sucrose formed per minute per mg of protein at 37° C. In a more preferred embodiment, the protein will demonstrate even more improved sA and increased purification factors (see, Table 1).

The invention relates to the enzyme comprising a corn SPS having a molecular weight from about 110 to 130 kilodalton (kd) and a specific activity of greater than 0,05 U.

The invention relates more particularly to the enzyme comprising a corn SPS having a specific activity of about 25 U.

In order to obtain the nucleic acid sequences encoding the SPS, especially corn SPS, substantially purified SPS was required. As demonstrated more fully in the examples, corn SPS purified 500-fold was obtained in small quantities which were then ultimately used to obtain peptide sequence which in turn led to the determination of the cDNA sequence.

Among the preferred proteins of the invention are the proteins having the above definition with a molecular weight from about 110 to about 130 kd, having the form of a monomer, a dimer or a tetramer and their derivatives, comprising at least one peptide having the following amino acid sequence:

Thr-Trp-Ile-Lys (SEQ ID NO: 1)
Tyr-Val-Val-Glu-Leu-Ala-Arg (SEQ ID NO: 2)
Ser-Met-Pro-Pro-Ile-Trp-Ala-Glu-Val-Met-Arg (SEQ ID NO: 5)
Leu-Arg-Pro-Asp-Gln-Asp-Tyr-Leu-Met-His-Ile-Ser-His-Arg (SEQ ID NO: 4)
Trp-Ser-His-Asp-Gly-Ala-Arg (SEQ ID NO: 5)

The invention also relates to a process to prepare proteins as above defined, characterized in that:
a) one extracts from parts containing SPS, preserved at low temperature, by grinding, centrifugation and filtration,
b) one increases the SPS rate of the extract so obtained by precipitation in an appropriate solvent, centrifugation and solubilization of the precipitate in a buffer solution.
c) one purifies the protein so obtained by chromatography and if desired,
d) one prepares the hybridomas, and monoclonal antibodies from an antigenic solution prepared from one of the preparations a, b, c,
e) one screens the hybridomas and raises monoclonal antibodies specifically directed against SPS,
f) one purifies the SPS so obtained with the monoclonal antibodies bodies so prepared.

The invention more precisely relates to a process of preparation of corn SPS characterized in that:
a) one extracts from part of corn plants by grinding centrifugation and filtration,
b) one increases the SPS rate of the extract so obtained by precipitation in polyethyleneglycol (PEG), centrifugation and solubilization of the precipitate obtained in a buffer solution,
c) one purifies the protein obtained in low pressure anion exchange chromatography and in chromatography on heparin sepharose, then in anion exchange high performance chromatography,
d) one purifies the active pools by passage on 2 high performance chromatography columns, and if desired,
e) one prepares the hybridomas and monoclonal antibodies from an antigenic solution prepared from one preparation a, b, c,
f) one screens the hybridomas and raises the monoclonal antibodies specifically directed against SPS,
g) one purifies the SPS preparation with the monoclonal antibodies so obtained.

Preferably:
- corn is a corn Pioneer corn hybrid strain 3184,
- part of plants are leaves kept at low temperature by example between −50° C. and −90° C.,
- purification in the polyethyleneglycol is realized
  . first by precipitating at a final concentration in PEG about 6%,
  . then by precipitating at a final concentration about 12%.

The different chromatographies are realized in the following way:
1st chromatography DEAE sepharose
2nd chromatography heparin sepharose: at this stage, the preparation obtained may be kept several days without loss of activity
3rd chromatography Mono q chromatography
4th chromatography HPLC hydroxyapatite
5th chromatography HPLC hydroxyapatite.
- during the different steps of purification and thereafter, the SPS activity may be measured according to two methods,
a) a method based on a colorimetric test or resorcinol test,
b) a method based on the dosage of one of the products formed during the transformation reactions where SPS is involved.

Both methods are detailed in the experimental part detailed hereunder.

Mice are immunized with several injections of enzymatic preparations.

Different kinds of mice may be used, for example BALB/c.

The antigen may be used in completed Freund adjuvant then in incompleted Freund adjuvant. Several injections in mice are realized: good results have been obtained with three injections of Mono q, pools, followed by three injections of final pools (days 0, 14, 27, 60, 90 and 105 for example).

The first injections are administered sub-cutaneously, for example in the cushions, and the feet, the last injection is administered intravenously in the tail for example.
- the preparation of spleen cellular suspensions so immunized is made in a conventional way.

The steps of fusion with myelona cells, of conservation of the hybridoma, of cloning, of antibodies production are made by conventional ways.

To detect the hybridoma secreting the monoclonal antibodies raised against the antigen, two methods are used to select antibodies:
  . a method of detection of antibodies as inhibitor of SPS activity,
  . a method of detection of antibodies precipitating SPS activities.

In a preferred embodiment, these methods are the methods described in the experimental section detailed hereunder.

Among the objects of the invention, are also provided lines of hybridoma cells, and in particular hybridoma cells described as:

| | |
|---|---|
| SPA 2-2-3:I-971 | SPB 3-2-19:I-973 |
| SPA 2-2-22:I-970 | SPB 5-2-10:I-974 |
| SPA 2-2-25:I-972 | SPB 5-4-2:I-975 |
| | SPB 13-1-7:I-976 |
| | SPB 13-2-2:I-977 | a deposit of which has been made at the C.N.C.M. (INSTITUT PASTEUR PARIS) on Jun. 11, 1990.

The invention relates also to monoclonal antibodies specifically directed against SPS.

The invention relates also to a process of preparation of proteins as defined above characterized in that a preparation containing the socalled proteins is purified on a chromatography column having monoclonal antibodies as defined above specifically raised against the proteins.

The invention relates also to cDNA coding for proteins as defined above, specially cDNA coding for corn SPS. Among the preferred cDNA preferred is the cDNA with the following nucleotide sequence (SEQ ID NO: 6) represented in FIG. 7A through FIG. 7J.

Thus, this invention relates to an extrachromosomal DNA sequence encoding a SPS as defined above. Any DNA sequence which is not incorporated into the genome of a plant is considered extrachromosomal, i.e., outside of the chromosome, for purposes of this invention. This includes, but is not limited to cDNA, genomic DNA, truncated sequences, single stranded and double stranded DNA. In a preferred embodiment, the DNA sequence is cDNA. In a different preferred embodiment, the DNA sequence is obtainable from corn.

Figure 1:
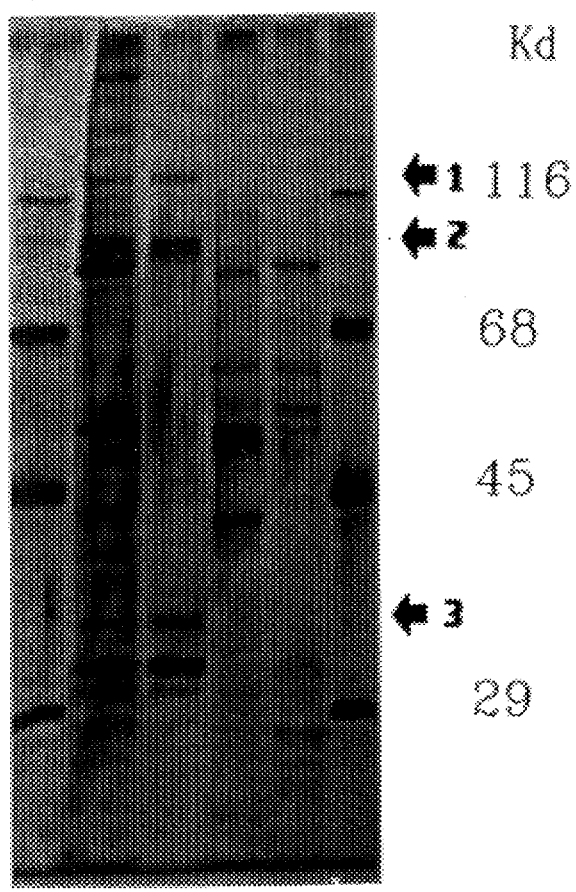
FIG. 1 shows an SDS-PAGE profile at various stages of SPS purification and the quality of the final preparation. See Section 1.2.7 for Key to FIG. 1.

Among the preferred proteins and nucleic acid sequences of the invention is corn SPS. The corn SPS is represented in FIG. 1, which shows the presence of proteins at about 120, 95 and 30 kd. The proteins shown at 95 and 30 kd are considered to be breakdown products of the protein shown at 120 kd. The complete protein is believed to a a di- or tetrameric protein having as the basic sub-unit from about a 110 to about 130 kd protein. The complete cDNA sequence (SEQ ID NO: 6) of the corn SPS is shown in FIG. 7.

cDNA coding for sucrose phosphate synthase has been prepared in the following way.

1) Sequencing of peptide fragments from purified SPS.

With the purified preparations of SPS previously obtained, by separating on acrylamide gel, a 120 kd minor band (corresponding to the total protein sequence) and two 90 kd and 30 kd major bands are obtained. Both major polypeptides are separated on electrophoresis and electroeluted. By a trypsin digestion and the sequencing of fragments so obtained, the sequence of 5 peptides has been determined.

This aminoacid sequence allows to determine the corresponding degenerate nucleotide sequence.

2) Corn leaf isolation.

Total RNA is isolated according to TURPEN and GRIFFITH (1986, Biotechniques vol. 4 pages 11–15) for poly(A) RNA preparation, the standard oligo dT cellulose column was used.

3) cDNA library construction.

cDNA synthesis is realized by following the protocol of a kit supplied by PROMEGA except that M-MLV reverse transcriptase is used instead of AMV reverse transcriptase. The length of cDNA obtained is from 500 to several thousand base pairs. One adds ECORI linkers to the blunt ended cDNA and clones this material into a second generation lambda GT11 expression vector. Total library size is about $1,5.10^6$ plaques.

4) Utilization of PCR in order to synthesize a nucleotide sequence specific for SPS.

The oligonucleotides derived from peptides B11 (SEQ ID NO: 3) (SPS 30 kd) and 4K (SEQ ID NO: 4) (90 kd) described in FIG. 3 are used as primers in a PCR reaction. It has been assumed that peptides derived from SPS 30 and SPS 90 are degradation products of protein SPS 120 kd, and that, peptides derived from SPS and SPS 90 are encoded by the same RNA.

With this hypothesis, by using in proper polarity pairs of oligonucleotides corresponding to the peptidic sequences in a PCR reaction, one may obtain the synthesis of the DNA, connecting the two location. Since it is a priori not known in which order the peptides are located relative to each other, one has to do the two different possibilites FIG. 4. Only the oligonucleotide couple CD3 synthesizes a cDNA of defined length (1200 bp) (FIG. 5A and FIG. 5B).

5) cDNA libray screening.

When 250000 lambda clones GT11 are screened using the 1200 bp long PCR cDNA, 16 positives are obtained. Sizes of the inserts ranged from 0,3 kb to 2,8 kb (see FIG. 6 for the two longest clones). The sequence is not complete in 5'. In a second round of library screening with a 400 bp DNA fragment corresponding to the most 5' fragment of the clone SPS 3, we obtain a SPS 61 clone extending further 5' without having the 5' end of the reading frame (FIG. 6).

6) Creation and screening of a second cDNA library in order to clone the 5' sequence of cDNA coding for SPS.

A oligonucleotide complementary to the 5' sequence of clone SPS 61 is used as a primer for cDNA synthesis. After second strand reaction is completed, the cDNA is cloned into bacteriophage lambda GT11. The library includes about one million clones. The SPS 90 and SP 77 have been obtained, by screening this library with SPS 61 (FIG. 6).

7) The assembled SPS reading frame.

DNA sequences which encode the SPS may be employed as a gene of interest in a DNA construct or as probes in accordance with this invention. When found in a host cell, the sequence may be expressed as a source of SPS. More preferred is the SPS sequence in a vegetal cell under the regulating control of transcriptional and translational initiation region functional in plants.

Vegetal cell means any plant cell being able to form undifferentiated tissues as callus or differentiated tissues as embryos, parts of plants, whole plants or seeds.

Plants means for example plant producing grain seeds for example such as cereals, such as wheat, barley, corn, or oat, leguminous such as soybean, oleaginous as turnesol, tuber as potato, plan with roots as beet or fruit as tomato. The sucrose phosphate synthase is a key enzyme, in sucrose regulation mechanisms, but also in carbon partitioning regulation between starch and sucrose during photosynthesis (see Jack PREISS, TIBS January 1984, page 24, or Mark STITT and Coll, BIOCHEMISTRY of PLANTS, vol. 10, 1987, pages 3–27).

When found in a DNA construct for integration into a plant genome, the sequence may be found is a sense orientation or anti-sense orientation. By increasing the amount of SPS available to the photosynthetically active plant cell by the expression of additional SPS, an increased flow of sucrose may be provided to growing tissues, for example, resulting in increased plant yields; by decreasing the amount of SPS available to the photosynthetically active plant cell, the rate of sucrose release from the plant cell may be hindered, resulting in less new plant growth.

By "obtainable from corn" is meant that the sequence, whether an amino acid sequence or nucleic acide sequence, is related to a corn SPS, including a SPS recovered through use of nucleic acid probes, antibody preparations, sequence comparisons or derivatives obtained through protein modeling or mutagenesis for example. Thus, one skilled in the art will readily recognize that antibody preparation, nucleic acid probes (DNA and RNA) and the like may be prepared and used to screen and recover other plant sources for SPS. Typically, a homologously related nucleic acid sequence will show at least about 60% homology, and more preferably at least about 70% homology between the corn SPS and the given plant SPS of interest, excluding any deletions which may be present. Homology is found when there is an identity of base pairs an may be determined upon comparison of sequence information, nucleic acid or amino acid, or through hybridization reactions conducted under relatively stringent conditions, e.g., having a fairly low percentage of non-specific binding with corn SPS probes.

Probes can be considerably shorter than the entire sequence, but should be at least about 10, preferably at least about 15, more preferably at least 20 nucleotides in length. Longer oligonucleotides are also useful, up to the full length of the gene encoding the polypeptide of interest. Both DNA and RNA probes can be used.

A genomic library prepared from the plant source of interest may be probed with conserved sequences from corn SPS to identify homologously related sequences. Use of the entire corn SPS cDNA may be employed if shorter probe sequences are not identified. Positive clones are then analyzed by restriction enzyme digestion and/or sequencing. In this general manner, one or more sequences may be identified providing both the coding region, as well as the transcriptional regulatory elements of the SPS gene from such plant source.

In use, probes are typically labeled in a detectable manner (for example with $^{32}$P-labelled or biotinylated nucleotides) and are incubated with single-stranded DNA or RNA from the plant source in which the gene is sought, although unlabeled oligonucleotides are also useful. Hybridization is detected by means of the label after single-stranded and double-stranded (hybridized) DNA or DNA/RNA have been separated, typically using nitrocellulose paper or nylon membranes. Hybridization techniques suitable for use with oligonucleotides are well known to those skilled in the art.

From cDNA sequences, one skilled in the art will be readily able to obtain the corresponding genomic DNA sequences related thereto to obtain the coding region of the SPS including intron sequences, transcription, translation initiation regions and/or transcript termination regions of the respective SPS gene. The regulatory regions may be used with or without the SPS gene in various probes and/or constructs.

The complete SPS reading frame can be assembled using restriction enzyme fragments of SPS 90, SPS 61 and SPS 3, see FIG. 6.

When expressed in *E. coli*, the SPS cDNA produces a protein which is recognized by anti SPS antisera and has the same electrophoretic mobility as SPS extracted from corn leaves. We show that this *E. coli* SPS is as active as plant SPS, i.e. for complete enzymatic activity in *E. coli* no other plant factor is needed but the SPS cDNA.

Plants obtained by the method of transformation and containing fusions of SPS cDNA to tissue specific promoters in order to modify or alter the composition of certain plant organs is also included.

A DNA construct of this invention may include transcriptional and translational initiation regulatory regions homologous or heterologous to the plant host. Of particular interest are transcriptional initiation regions from genes which are present in the plant host species, for example, the tobacco ribulose biphosphate carboxylase small subunit (ssu) transcriptional initiation region; the cauliflower mosaic virus (CaMV) 35S transcriptional initiation region, including a "double" 35S CaMV promoter; and those associated with T-DNA, such as the opine synthase transcriptional initiation region, e.g., octopine, mannopine, agropine, and the like.

Any one of number of regulatory sequences may be preferred in a particular situation, depending upon whether constitutive or tissue and or timing induced transcription is desired, the particular efficiency of the promoter in conjunction with the heterologous SPS, the ability to join a strong promoter with a control region from a different promoter which allows for inducible transcription, ease of construction and the like. For example, tissue specific promoters may be employed to selectively modify or alter the composition of certain plant organs. These regulatory regions find ample precedence in the literature.

The termination region may be derived from the 3'-region of the gene from which the initiation region was obtained, from the SPS gene, or from a different gene. Preferably the termination region will be derived from a plant gene, particularly, the tobacco ribulose biphosphate carboxylase small subunit termination region; a gene associated with the Ti-plasmid such as the octopine synthase termination region or the tml termination region.

In developing the expression cassette, the various fragments comprising the regulatory regions and open reading frame may be subjected to different processing conditions, such a ligation, restriction, resection, in vitro mutagenesis, primer repair, use of linkers and adapters, and the like. Thus, nucleotide transitions, transversions, insertions, deletions, or the like, may be performed on the DNA which is employed in the regulatory regions and/or open reading frame.

During the construction of the expression cassette, the various fragments of the DNA will usually be cloned in an appropriate cloning vector, which allows for amplification of the DNA, modification of the DNA or manipulation by Joining or removing of the sequences, linkers, or the like. Normally, the vectors will be capable of replication in at least a relatively high copy number in *E. coli*. A number of vectors are readily available for cloning, including such vectors as pBR322, pUC series, M13 series, etc. The cloning vector will have one or more markers which provide for selection of transformants. The markers will normally provide for resistance to cytotoxic agents such as antibiotics, heavy metals, toxins, or the like. By appropriate restriction of the vector and cassette, and as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate.

The manner of transformation of *E. coli* with the various DNA constructs (plasmids and viruses) for cloning is not critical to this invention. Conjugation, transduction, transfection or transformation, for example, calcium phosphate mediated transformation, may be employed.

In addition to the expression cassette, depending upon the manner of introduction of the expression cassette into the plant cell, other DNA sequences may be required. For example when using the Ti- or Ri-plasmid for transformation of plant cells, as described below, at least the right border and frequently both the right and left borders of the T-DNA of the Ti- or Ri-plasmids will be Joined as flanking regions to the expression cassette. The use of T-DNA for transformation of plant cells has received extensive study and is amply described in *Genetic Engineering, Principles* and Methods (1984) Vol 6 (Eds. Setlow and Hollaender) pp. 253–278 (Plenum, N.Y.); A. Hoekema, in: *The Binary Plant Vector System* (1985) Offsetdrukkerij Kanters, B. V. Alblasserdam.

Alternatively, to enhance integration into the plant genome, terminal repeats of transposons may be used as borders in conjunction with a transposase. In this situation, expression of the transposase should be inducible, so that once the expression cassette is integrated into the genome, it should be relatively stably integrated and avoid hopping.

The expression cassette will normally be joined to a marker for selection in plant cells. Conveniently, the marker may be resistance to a biocide, particularly an antibiotic, such as Kanamycin, G418, Bleomycin, Hygromycin, Chloramphenicol, or the like. The particular marker employed will be one which will allow for selection of transformed plant cells as compared to plant cells lacking the DNA which has been introduced.

A variety of techniques are available for the introduction of DNA into a plant cell host. These techniques include transformation with Ti-DNA employing *A. tumefaciens* or *A. rhizogenes* as the transforming agent, protoplast fusion, injection, electroporation, DNA particle bombardment, and the like. For transformation with agrobacterium, plasmids can be prepared in E. coli which plasmids contain DNA homologous with the Ti-plasmid, particularly T-DNA. The plasmid may be capable of replication in Agrobacterium, by inclusion of a broad spectrum prokaryotic replication system, for example RK290, if it is desired to retain the expression cassette on a independent plasmid rather than having it integrated into the Ti-plasmid. By means of a helper plasmid, the expression cassette may be transferred to the *A. tumefaciens* and the resulting transformed organism used for transforming plant cells.

Conveniently, explants may be cultivated with the *A. tumefaciens* or *A. rhizogenes* to allow for transfer of the expression cassette to the plant cells, the plant cells dispersed in an appropriate selection medium. The Agrobacterium host will contain a plasmid having the virgenes necessary for transfer.

After transformation, the cell tissue (for example protoplasts, explants or cotyledons) is transferred to a regeneration medium, such as Murashige-Skoog (MS) medium for plant tissue and cell culture, for formation of a callus. Cells which have been transformed may be grown into plants in accordance with conventional ways. See, for example, McCormick et al., *Plant Cell Reports* (1986) 5:81–84. The transformed plants may then be analyzed to determine whether the desired gene product is still being produced in all or a portion of the plant cells. After expression of the desired product has been demonstrated in the plant, the plant can be grown, and either pollinated with the same transformed strain or different strains and the resulting hybrid having the desired phenotypic characteristic identified. Two or more generations may be grown to ensure that the subject phenotypic characteristic is stably maintained and inherited.

1 - PURIFICATION OF SUCROSE PHOSPHATE SYNTHASE OF CORN 1.1 - Method of determination of enzymatic activity (SPS)
During purification SPS activity is followed in 2 ways:
a) either by means of a colorimetric test (P. S. Kerr et al., Planta., 1987, 170:515–519) called resorcinol test described below.

Sucrose Phosphate Synthase or UDP glucose - D Fructose - Phosphate Glucosyltransferase (EC 2.4.1.14) catalyzes the reaction:

UDPG+Fructose 6-P<=>Sucrose 6-P+UDP
UDPG: Uridine Di-Phospho Glucose
Fructose 6-P or F6P: Fructose 6-Phosphate
Sucrose 6-P: Sucrose 6-Phosphate The sucrose 6-P formed reacts with the Resorcinol to give a red-colored compound quantifiable by spectro-photometry at 520 nm (nanometer) (Optical Density (O.D.)=520 nm). In practice, to 45 μl (microliter) of enzymatic preparation 25 μl of a buffered solution containing the two substrates is added (UDPG 70 mM, F6P 28 mM, $MgCl_2$ 15 mM, HEPES 25 mM pH 7,5). After incubation at 37° C., reaction is stopped by adding 70 μl of NaOH in Solution and heating at 95° C. during 10 mn. After cooling, 0,25 ml of a solution 0,1% resorcinol in ethanol 95% is added, then 0,75 ml of HCl 30% is added. The OD 520 mM is read after incubation 8 mn at 80 mn, and cooling.

b) or by means of a coupled enzymatic system (S. Harbron et al., *Anal. Biochem.* 1980, 107: 56–59) being composed in the following way:

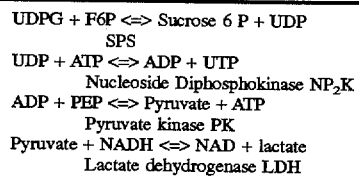

The disappearance of the NADH absorption at 340 nm is monitored 1 mole of NAD formed or 1 mole of NADH consumed corresponds to 1 mole of sucrose 6 P formed.

In practice, in a quartz spectrophotometric tun thermostated at 37° C., the following solution are added.
- 540 μl of HEPES buffered 50 mM, $MgCl_2$ 10 mM KCl 20 mM pH=7,5,
- 250 μl of a mixture of substrates PEP (1,6 mM NaDH 0,6 mM, ATP 4 mM UDPG 112 mM),
- 60 μl of an enzyme mixture (LDH 166,7 U/ml PK 333,3 U/ml, NPzK 66,7 U/ml),
- 100 μl of F6P 112 mM.

After homogenization, 50 μl of the preparation containing SPS is added, the diminution of optical density at 340 nm is added with a spectrophotometer (UVIKON 860, KONTRON instruments). The measure is done with the kinetic of the machine.

1.2 - Purification of the SPS (preparation of the immunogen)
1.2.1 - Extraction

The starting material for the purification are mature leaves of young corn plants (*Zea mays* L. cv Pioneer 3184), which have been harvested in late morning, cut up, deveined, frozen in liquid nitrogen and stored at −70° C.

250 g of leaves are suspended in 1 liter of 50 mM HEPES 10 mM $MgCl_2$ 1 mM EDTA 5 mM DTT, pH=7.5 buffer (extraction buffer) which has observed to it 11 g of Polyvinyl-pyrrolidone nitrogen is bubbled through and the suspension is cooled to 0° C.

The leaves are ground, until a homogeneous liquid is obtained. This ground product is filtered, and then centrifuged at 14,000 g for 20 minutes at 4° C.

While the bubbling through of nitrogen is maintained, a solution of 50% Poly Ethylene Glycol (PEG 8000 "Breox" at 50% w/v of extraction buffer) is added to the supernatant until a final concentration of PEG of 6% is reached. Then the suspension is cooled at 0° C. After centrifuging at 14,000 g for 20 minutes the supernatant has added to it 50% PEG until a final concentration of PEG of 12% is reached. After a repeated centrifugation, the supernatant is discarded and the residue is solubilized with 60 ml of 50 mM HEPES, 10 mM MgCl$_2$, 1 mM EDTA, 5 mM DTT, 10% Ethylene Glycol (EG), 0.08M KCl, pH 7.5 buffer (recovery buffer). This solution is clarified by centrifuging at 40,000 g for 10 minutes. The supernatant constitutes the final extract.

1.2.2 - Low pressure anion-exchange chromatography: fast-flow DEAE Sepharose exchanger The final extract is chromatographed on a column 25 mm×162 mm of 80 ml of Fast-Flow DEAE Sepharose PHARMACIA equilibrated with recovery buffer. After washing the column with the same buffer, the proteins adsorbed on the support are eluted by means of a linear gradient with increasing ionic strength between 0.08M KCl and 0.35M KCl in the 50 mM HEPES, 10 mM MgCl$_2$, 1 mM EDTA, 5 mM DTT, 10% EG, pH 7.5 buffer (buffer A). The flow rate applied during this experiment is 180 ml/h and chromatography is executed at 4° C.

The SPS activity is eluted at about 0.17M KCl.

1.2.3 - Chromatography on heparin Sepharose

The fractions containing the SPS activity are collected and diluted to one fifth in buffer A, then added to 12 ml of heparin Sepharose previously equilibrated with buffer A. After one hour of incubation with gentle agitation at 4° C., the gel is washed with about 10 volumes of buffer A+0.05M KCl, then repacked in a chromatography column.

The proteins adsorbed are eluted in an isocratic way by means of a 10 mM CAPS, 10 mM MgCl$_2$, 1 mM EDTA, 5 mM DTT, 10% EG, 0.01% Tween 80, 1 mg/ml heparin, 1% Fructose, 0.25M KCl, pH 10 buffer, delivered at 60 ml/h.

Chromatography is executed at 4° C.

The fractions containing the SPS activity are collected (heparin fraction) and preserved on ice until the following purification stage. The enzyme at this stage is stable for a least one week.

The following purification steps are carried out using a system of High Performance Liquid Chromatography (HPLC); the purification is followed by means of a detector fitted with a filter enabling absorbency in the ultra-violet at 280 nm (A280) to be measured. The buffers and the fractions recovered are kept at low temperature.

1.2.4 - High performance anion-exchange chromatography: Mono Q

The heparin fraction is diluted by adding one third volume of 20 mM Triethanolamine, 10 mM MgCl$_2$, 1 mM EDTA, 10 mM DTT, 3% EG, 0.3% Tween 80, pH 7.5 buffer (buffer A) and loaded on an FPLC Mono Q HR10/10 column, (10×100 mm PHARMACIA) previously equilibrated with the same buffer which has added to it NaCl (final concentration 0.18M). After the A280 has returned to 0, the proteins adsorbed on the chromatography support are eluted by means of a salt-complex gradient comprised as follows:

buffer A: cf above
buffer B: buffer A+NaCl 1M

| time (minutes) | % B |
| --- | --- |
| 0 | 18 |
| 0.1 | 24 |
| 15 | 24 |
| 19 | 26 |
| 23 | 26 |
| 33 | 31 |
| 38 | 31 |
| 41 | 100 |
| 43 | 18 |

The flow rate applied to the column is 180 ml/h.
The SPS activity is eluted between 0.26 and 0.31M NaCl.
The active fractions are collected together ("Mono Q fraction").

1.2.5 - HPLC on Hydroxyapatite

The Mono Q fraction is loaded on an HPLC column of hydroxyapatite 4 mm×75 mm neutralized with 20 mM KH$_2$PO$_4$/K$_2$HPO$_4$, 3% EG, 0.3% Tween 80, 5 mM DTT, pH 7.5 buffer. After the A280 has returned to 0, the proteins adsorbed are eluted by means of the following phosphate gradient:

buffer A: cf above
buffer B: idem buffer A but 500 mM Phosphate of K

| time (minutes) | % B |
| --- | --- |
| 0 | 2 |
| 5 | 11 |
| 9 | 13 |
| 14 | 13 |
| 29 | 40 |
| 31 | 100 |
| 32 | 100 |
| 35 | 2 |

The flow rate applied is 60 ml/h. At this stage, the phosphate will partially inhibit SPS activity and therefore it is difficult to calculate a specific activity and also a purification factor (cf table 1) at this stage.

The SPS activity is eluted under these conditions with about 60 mM phosphate.

The active fractions are collected together and constitute the HAC fraction.

1.2.6 - HPLC on DEAE 5PW

The HAC fraction is loaded on an anion-exchange HPLC column of Di Ethyl Amino Ethyl type (DEAE-SPW) previously neutralized with a buffer of 20 mM Triethanolamine, 10 mM MgCl$_2$, 1 mM EDTA, 3% EG, 2.5 mM DTT, 2% betaine, pH 7.5 buffer (buffer A)+0.15M NaCl.

After the A280 has returned to 0, the proteins adsorbed are eluted by means of the following NaCl gradient:

buffer A: cf above
buffer B: idem buffer A with 1M NaCl

| time (minutes) | % B |
| --- | --- |
| 0 | 15 |
| 0.1 | 20 |
| 5 | 20 |
| 22 | 35 |
| 27 | 35 |
| 30 | 100 |
| 31 | 15 |

The flow rate used is 60 ml/h.
The SPS activity is eluted with about 0.3M NaCl.

1.2.7 - Preparation of the final preparation: concentration

The final preparation is concentrated by HPLC chromatography on Mono Q HR5/5 exchanger (5×50 mm, Pharmacia) and rapid elution.

The DEAE 5PW fraction (or the G200 fraction) is diluted to two thirds with buffer A (idem 6) and loaded on the column previously neutralized with buffer A+0.18M NaCl. The following gradient is then applied on the column:

buffers A and B: idem 6

| time (minutes) | % B |
| --- | --- |
| 0 | 18 |
| 10 | 40 |
| 12 | 100 |
| 13 | 18 |

The flow rate used is 60 ml/h.

The SPS activity is eluted with about 0.3M NaCl.

The final preparation is stored at −20° C. until used. Table 1 summarizes the results obtained at the various purification stages in terms of quantities of proteins recovered and of SPS activity.

TABLE 1

|  | Concentration of proteins (mg/ml) | Volume (ml) | sA (U) | pF | Y* (%) |
|---|---|---|---|---|---|
| Ground product | 1 | 1000 | 0.05 | 0 | 100 |
| Final extract | 4< <8 | 60 | 0.30 | 6 | 144 |
| DEAE FF fraction | 0.4< <0.8 | 70 | 3 | 60 | 168 |
| Heparin fraction | 0.2< <0.4 | 25 | 9 | 180 | 90 |
| Mono Q fraction | (0.02) | 30 | — | — | — |
| HAC fraction | (0.03) | 8 | — | — | — |
| Final preparation | 0.05 | 2 | 25 | 500 | 5 |

Key
sA = Specific enzymatic activity:1 U corresponds to 1 μm of sucrose formed per minute per mg of protein at 37° C.
pF = Purification factor
Y = Yield
( ) = approximate value
— = not determined Observations: ** the measurement of the quantity of proteins is carried out using the Bradford method. As Tween interferes enormously with this method, it is not possible to determine the proteins and then to calculate an sA at the level of the stages containing one. Furthermore, as phosphate is an inhibitor of SPS activity, the determination during the HAC stage gives an underestimated result.
* the increasing yield during the initial stages can be explained by the elimination, during purification, of certain inhibitors of SPS activity.

An SDS-PAGE profile at various stages of the purification process and the quality of the final preparation is given in FIG. 1. The 120, 95 and 35 kd proteins are correlated to the SPS activity.

The 35 and 95 kd proteins are very likely breakdown products of the 120 kd protein as it can be shown by the nucleotidic sequence coding for the SPS protein.

Furthermore, the antibodies directed against the 35 and 95 kd proteins also recognize the protein 120 kd in immunodetection after membrane transfer, which demonstrates an antigenic identity between these three proteins (see below). It must be pointed out, however, that the addition of protease inhibitors in the buffers during purification has not enabled us to obtain a single 120 kd protein.

Gel permeation chromatographies were carried out in order to find the apparent molecular weight of the native SPS protein. Briefly, the HAC fraction is concentrated by HPLC chromatography on Mono Q HR 5/5 inchanger (see 1-2-7). The active fractions are collected together (about 2 ml) and loaded on an G 200 column previously washed with a buffer containing 20 mM triethanolamin, 10 mM MgCl$_2$, 1 mM EDTA, 3% E.G., 2,5 mM DTT, 2% betain, 0,3M NaCl pH 7,5. The SPS activity is eluted a major protein peak corresponding to an apparent mass of 270–280 kda which is in agreement with the results obtained by S. HARBRON an al. (*Arch. Biochem. Biophys.*, 1981, 212: 237–246) with the spinach SPS. It can be noted that the chromatography on a TS lambda 60000 permeation column lead to the elution of the SPS activity at a retention time corresponding to an apparent mass of 440 kda which is near from the value obtained by DC. DOEHLERT and S. C. HUBER (*Plant Physiol.*, 1983, 73:989–994) with the spinach SPS, using a AcA34 permeation column.

The SPS protein seems therefore to be a di or tetrameric protein having as the basic sub-unit a 120 kda protein (homo-dimeric or homo-tetrameric).

Key for FIG. 1

SDS-PAGE profile of sucrose phosphate synthase of corn: 8.5% acrylamide gel, reducing conditions and staining with silver nitrate M: Standard of molecular weight B-Galactosidase (116 kd), bovine Albumin (68 kd), Egg Albumin (45 kd), carbonic Anhydrase (29 kd).

H: Heparin fraction, 30 micrograms of proteins per well.

FP: Final Preparation, 7.5 micrograms of proteins per well.

FE: Final Extract, 7.5 micrograms of proteins per well.

D: Fast-Flow DEAE fraction, 7.5 micrograms of proteins per well.

The bands of proteins visible at about 120 kd (1), 95 kd (2) and 35 kd (3) are correlated, during the chromatography stages, with the appearance of SPS activity in the respective fractions.

2 - PROCESS FOR THE PREPARATION OF MONOCLONAL ANTIBODIES DIRECTED AGAINST SUCROSE PHOSPHATE SYNTHASE 2.1 - Immunisations BALB/C mice are immunized by subcutaneous injection (pads and paws) according to the following methodology:

Day 0 injection of about 5 micrograms of proteins (or about 0.3 U SPS per mouse): Mono Q pool emulsified volume for volume with Freund's Complete Adjuvant (FCA).

Day 14 injection of about 5 micrograms of proteins (or about 0.3 U SPS per mouse): Mono Q pool emulsified volume for volume with Freund's Incomplete Adjuvant (FIA).

Day 27 Idem D14

Day 0+60 injection of about 20 micrograms of proteins: final pool in FIA

Day 0+90 injection of about 12 micrograms of proteins: final pool in FIA

Day 0+135 injection by intravenous route (IV) in the tail of about 20 micrograms of proteins: final pool.

Fusion is achieved 3 days after the IV immunisation.

The sera are removed at D34, D61, D98 and D159 in order to measure the immunitary response (cf screening).

2.1.1 - Screening method

As the SPS used for the immunisations is not perfectly homogeneous, it is necessary to establish a screening test specific to this enzyme.

Two methods for the detection of the antibodies are used:
- detection method of antibodies inhibiting the SPS activity
- detection method of antibodies directed against the SPS (inhibiting or not).

a) Detection method of antibodies inhibiting the SPS activity
  This method of screening allows the detection of antibodies which interfere with the active site of the SPS or on a site close to the latter, and therefore prevent the access of substrates. In practice, 70 μl of serum or of supernatant of hybridoma culture diluted in a suitable way is mixed with 70 μl of SPS preparation (Heparin fraction). After one hour of incubation at ambient temperature, the residual SPS activity is determined by coupled enzymatic determination (Cf 1—1). The results are expressed as a percentage of inhibition as compared to the same SPS preparation treated in the same way but without antibodies.

b) Detection method of antibodies directed against SPS (inhibiting or not)
  This method is based on the precipitation of the antibody-SPS complex by goat anti-mouse IgG coupled to sepharose beads (GAM sepharose). In practice, 60 μl of serum or supernatant of hybridoma culture diluted in any suitable manner is added to 60 μl of SPS preparation (Heparin fraction). After 2 hours of incubation at ambient temperature, the mixture is added to 50 μl of 25% GAM-Sepharose previously washed three times with a buffer of 50 mM HEPES, 10 mM $MgCl_2$, 1 mM EDTA, 10% EG, 5 mM DTT, pH 7.5. The mixture is incubated over night at 4° C. under strong agitation. After centrifuging for 5 minutes at 3000 rpm the residual SPS activity in the supernatant is determined by coupled enzymatic determination (Cf 1.1). The results are expressed as a percentage of precipitation (% prec.) compared to the same SPS preparation treated in the same way without antibodies.

2.1.2 - Results 10 mice were immunized according to the protocol described previously. The following table gives the results of the precipitation determinations carried out with the heteroantisera of the 10 mice on D159. The sera are diluted to one two-hundredth.

| MOUSE | 1 | 2 | 3 | 4 | 5 | 6 | 7 | 8 | 9 | 10 |
|---|---|---|---|---|---|---|---|---|---|---|
| % PREC. | 45 | 22 | 32 | 64 | 36 | 30 | 22 | 16 | 39 | 37 |

Additional dilutions of the serum of mouse 4 give the following results:

| DILUTION | % PRECIPITATION |
|---|---|
| 1/200 | 67 |
| 1/400 | 48 |
| 1/600 | 29 |
| 1/1000 | 20 |

The spleens of mice 1 and 4 are used for the fusion.

2.2 - Cellular fusion

The splenocytes of the mice are fused with myeloma cells of SP2/0-Ag14 mice according to a ratio of 2/1 in the presence of 45% polyethylene glycol 1500. The selection of the hybridomas is effected by adding hypoxanthine and azaserine to the culture medium 24 and 48 hours after fusion.

The hybridomas are cloned and sub-cloned by the method of limited dilution.

2.2.1 - Results of the screening of hybrids and clones.

HYBRIDS

| MOUSE 4 (SPA fusion) | MOUSE 1 (SPB fusion) |
|---|---|
| 2 postive hybrids | 6 positive hybrids |
| out of 45 | out of 52 |
| SPA2: 38% prec. | SPB3: 17% prec. |
| SPA19: 7% prec. | SPB5: 67% prec. |
| | SPB8: 53% prec. |
| | SPB13: 68% prec. |
| | SPB25: 13% prec. |
| | SPB34: 17% prec. |

CLONES

| SPA FUSION | SPB FUSION |
|---|---|
| 2 clones retained | 7 clones retained |
| out of 36 | out of 46 |
| SPA2-2: 85% prec. | SPB3-2: 19% prec. |
| SPA19-7: 8% prec. | SPB5-1: 76% prec. |
| | SPB5-2: 71% prec. |
| | SPB5-3: 45% prec. |
| | SPB5-4: 24% prec. |
| | SPB13-1: 79% prec. |
| | SPB13-2: 53% prec. |

SUB-CLONES

| SPA FUSION | SPB FUSION |
|---|---|
| 3 sub-clones retained | 5 sub-clones retained |
| out of 48 | out of 72 |
| SPA2-2-3: 60% prec. | SPB3-2-19: 21% prec. |
| SPA2-2-22: 33% prec. | SPB5-2-10: 86% prec. |
| SPA2-2-25: 92% prec. | SPB5-4-2: 46% prec. |
| | SPB13-1-7: 87% prec. |
| | SPB13-2-2: 93% prec. |

2.2.2 - Production of anti-SPS moncolonal antibodies

The hydridomas are injected by intra-peritoneal route into female BALB/C mice previously treated with pristane. The monoclonal antibodies are partially purified from ascital liquids thus produced by precipitation with 18% sodium sulphate. The proteins precipitated are dissolved then dialyzed against PBS (F18).

2.2.3 - Characterization of anti-SPS monoclonal antibodies a) Typing

The typing is done using an ELISA test. Anti-IgG rabbit and anti-IgM mouse antibodies (ZYMED) are fixed at the bottom of the wells of a 96-well plate. After one night at ambient temperature the unoccupied sites are saturated with a solution of 3% bovine serum albumin in PBS. After one hour of incubation at 37° C. and several washes, the various F18's are deposited in the wells. After incubation and several washes, goat or rabbit antibodies, anti-class and anti-sub class mouse immunoglobulins linked with peroxidase, are added. After one hour at 37° C., the antibodies are revealed using an $H_2O_2$/ABTS system.

All the anti-SPS monoclonal antibodies were found to be of Ig $G_1$ type.

b) Inhibition of SPS activity

The determination of the capacity of the antibodies to inhibit the SPS activity is carried out by the technique mentioned previously (Cf 2.1.1 a) using F18's.

| Antibody | Concentration of antibodies (micrograms/ml) | % Inhibition |
|---|---|---|
| SPA2-2-3 | 50 | 0 |
| SPA2-2-22 | 50 | 0 |
| SPA2-2-25 | 50 | 0 |
| SPB3-2-19 | 50 | 0 |
| SPB5-2-10 | 50 | 0 |
| SPB5-4-2 | 50 | 0 |
| SPB13-1-7 | 50 | 50 |
| | 25 | 55 |
| | 5 | 25 |
| | 2.5 | 10 |
| | 1 | 2.1 |

-continued

| Antibody | Concentration of antibodies (micrograms/ml) | % Inhibition |
|---|---|---|
| SPB13-2-2 | 50 | 60.1 |
| | 25 | 59.1 |
| | 5 | 33.8 |
| | 2.5 | 14.2 |
| | 1 | 8.7 | c) Immuno-precipitation of the SPS activity

The determination of the capacity of the antibodies to immuno-precipitate the SPS activity is carried out by the technique mentioned previously (Cf 2.1.1 b) using F18's.

| Antibody | Concentration of antibodies (micrograms/ml) | % Precipitation |
|---|---|---|
| SPA2-2-3 | 50 | 95 |
| | 25 | 92 |
| | 5 | 80 |
| | 2.5 | 40 |
| | 1 | 20 |
| SPA2-2-22 | 50 | 95.7 |
| | 25 | 95 |
| | 10 | 51 |
| | 5 | 48.2 |
| | 2.5 | 25 |
| | 1 | 10 |
| SPA2-2-25 | 50 | 91.3 |
| | 25 | 95.3 |
| | 5 | 90.4 |
| | 2.5 | 22.8 |
| | 1 | 12.5 |
| SPB3-2-19 | 50 | 95 |
| | 25 | 95 |
| | 5 | 27.8 |
| | 2.5 | 17.8 |
| | 1 | 9.3 |
| SPB5-2-10 | 50 | 95 |
| | 25 | 95 |
| | 5 | 81.1 |
| | 2.5 | 41.4 |
| | 1 | 22.6 |
| SPB5-4-2 | 50 | 95 |
| | 25 | 95 |
| | 5 | 86.1 |
| | 2.5 | 57.2 |
| | 1 | 26.1 |
| SPB13-1-7 | 50 | 95 |
| | 25 | 95 |
| | 10 | 65.4 |
| | 5 | 48.1 |
| | 2.5 | 15 |
| | 1 | 10 |
| SPB13-2-2 | 50 | 95 |
| | 25 | 95 |
| | 5 | 71.8 |
| | 2.5 | 43.5 |

3 - USE OF THE MONOCLONAL ANTIBODIES FOR THE CHARACTERIZATION AND PURIFICATION OF SUCROSE PHOSPHATE SYNTHASE 3.1 - Characterization of Corn Sucrose phosphate This characterization is carried out with SPB3-2-19 and SPB13-2-2 antibodies by the technique of immunodetection after transfer of the proteins from an electrophoresis gel under denaturing conditions (SDS-PAGE) on nitrocellulose membrane (western).

After electrophoretic separation in a 12.5% acrylamide gel (Nature 277 (1970) 680–685), the proteins are transferred onto a 0.22 μm nitrocellulose membrane (Schleicher and Schuell). The buffer is a standard electrophoresis buffer (3.03 g/l. TRIS base, 14.4 g/l. Glycine, 0.1% SDS, pH 8.3, 20% methanol).

Figure 2:
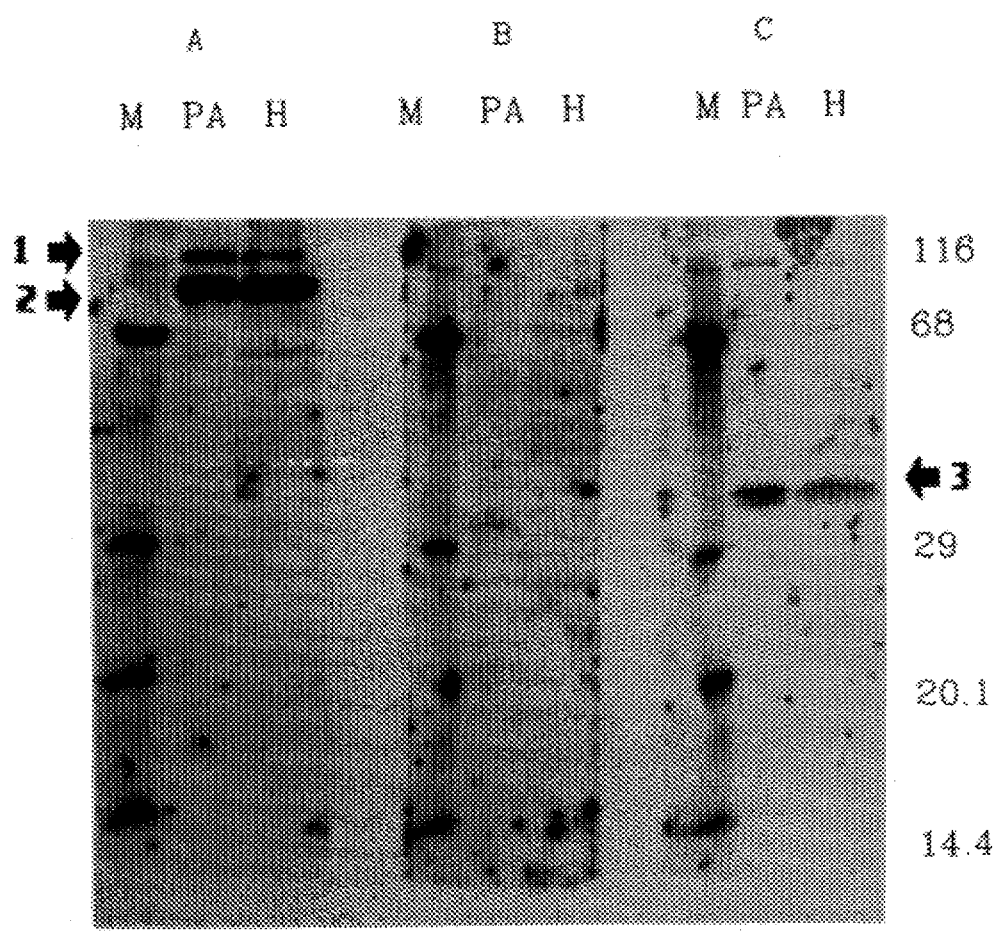
FIG. 2 shows the results of a Western analysis of SPS using monoclonal antibodies. See Section 3.1 for Key to FIG. 2.

After transfer, the membrane is put in a blocking bath (0.5% Casein in PBS). After one hour at 37° C. under gentle agitation, the membrane is washed 3 to 4 times in a washing buffer (0.1% Casein, 0.5% Tween 20, in PBS) then incubated with a solution of 10 micrograms/ml of the monoclonal antibody to be tested. A part of the membrane is incubated in parallel with a non-immune anti-body (negative control). After one hour of incubation at ambient temperature followed by 9 or 10 washes, the membrane is incubated in the presence of an anti-mouse antibody antibody labelled with Iodine 125 diluted in a washing buffer (50,000 cpm per $cm^2$ of membrane). After one hour of incubation at ambient temperature followed by 9 or 10 washes, the membrane is dried, then autoradiographed (X-OMAT AR KODAK film and Cronex XTRA Life DUPONT amplifying screen). An autoradiography is shown in FIG. 2. A strong signal is observed at the protein bands 120 kd, 95 kd and 35 kd which correlates with the previous results (see first part).

Key to FIG. 2

A: membrane incubated in the presence of the SPB3-2-19 antibody

B: membrane incubated in the presence of an antibody not directed against SPS (negative control anti-neomycin monoclonal antibody)

C: membrane incubated in the presence of the SPB13-2-2 antibody

M: standards of molecular weight radio-marked by 125I (NEX-188 NEN) B-Galactosidase (116 kd), bovine albumin (68 kd), carbonic Anhydrase (29 kd), trypsic Inhibitor (20.1 kd), Alpha-Lactalbumin (14.4 kd), 150,000 cpm per lane PA: proteins obtained after immunoaffinity chromatography (see below) with the SPB13-2-2 monoclonal antibody, about 40 micrograms of proteins per lane.

H: Heparin fraction, about 40 micrograms of proteins per lane.

3.2 - Purification of Sucrose Phosphate Synthase by immunoaffinity Chromatography A methodology for the purification of corn Sucrose Phosphate Synthase on an immunoaffinity support has been perfected in order to increase the quantity of protein recovered while reducing the number of purification stages and to obtain quantities sufficient for protein sequencing.

3.2.1 - Preparation of the immuno-adsorbent

The F18 (see 2.2.2) corresponding to the SPB13-1-7 antibody or to the SPB13-2-2 antibody were mixed with activated CH-Sepharose, (1 mg of antibody per ml of gel). After incubation for 2 hours at ambient temperature, the sites not occupied by the antibodies are saturated with 1M ethanolamine, pH 9. The support is then washed alternately with 0.1M acetate 0.5M NaCl pH 4 buffer and 0.1M TRIS 0.5M NaCl pH 8 buffer. The immunoaffinity support thus prepared is preserved at 4° C. in a 50 mM HEPES, 10 mM $MgCl_2$, 1 mM EDTA, 1 mM PMSF, 0.01% sodium nitride (azide), pH 7.5 buffer.

3.2.2 - Immunoaffinity Chromatography

50% PEG is added to the Heparin fraction of SPS (see 1.2.3.) is added 50% PEG (see 1.2.1) to a final concentration of PEG of 20%. After incubation for 30 minutes at 4° C. with gentle agitation, the mixture is centrifuged at 1600 g for 30 minutes. The protein deposit is taken up in half of the initial volume with the 50 mM HEPES, 10 mM $MgCl_2$, 1 mM EDTA, 10% ethylene glycol pH 7.5 buffer. This stage allows the previous buffer, which is incompatible with the immunoaffinity chromatography, to be eliminated, and the proteins to be concentrated. The yield of SPS activity is from 80 to 90%.

The solution obtained is applied with a flow rate of 0.1 ml/min over 1 ml of immunoaffinity support packed in a column and on which has been fixed an antibody not directed against the SPS (activated CNBr-Sepharose, on which an anti-neomycin antibody is fixed). This first stage allows the elimination of certain contaminants which are fixed non-specifically on the chromatography support. The effluent of the non-specific column is in its turn applied to the anti-SPS immunoaffinity support (2 ml in an 11×20 mm column) with a flow rate of 0.1 ml/min. These two stages are carried out at laboratory temperature. The column is washed with 10 ml of load buffer and then with a washing buffer (load buffer with the addition of 0.25M NaCl and 0.3% Tween 20) until absorbency in ultra-violet at 280 nm is close to base level. The proteins adsorbed on the support are eluted with a solution of 50 mM triethyl-amine, pH 11. This slution is carried out at 4° C. and the immunoaffinity column is reversed to obtain an optimum yield. The SDS-PAGE profile of the final preparation obtained corresponds to that obtained using the standard protocol (see 1). It must be noted that the slution method of the proteins adsorbed on the immunoaffinity support irrevesibly destroys the SPS activity but the recovery yield of the eluted SPS proteins is optimal compared to tests carried out in native slution conditions. The eluate of the immunoaffinity column is desalted with a Sephadex G25 column, against a 0.14% Glycerol, 0.07% 2-mercapto-ethanol, 0.04% SDS, 0.9 mM TRIS pH 6.8 buffer (electrophoresis buffer in reducing conditions diluted 70 times). After desalification, the protein preparation is concentrated 70 times with a concentrator under vacuum and the SPS proteins are purified by SDS-PAGE (see below).

4. Partial Sequencing of SPS Polypeptides

Samples of a purified protein preparation obtained as described in Example 3.2.2. were subjected to preparative SDS-PAGE. After electrophoresis, the protein bands were visualized with KCl treatment as described by Bergman and Joernvall (*Eur. Jour. Biochem.* (1978) 169:9–12) and the bands observed at 90 kd and 30 kd were excised. The proteins from these gel fragments were electroeluted using an Electrophoretic Concentrator according to manufacturer's instructions (ISCO; Lincoln, Neb.) in 4 mM sodium acetate, pH8. After electroelution, protein yields were quantitated by comparison to a bovine serum albumin (BSA) standard on a Coomassie Blue-stained gel. Approximately 30 μg of the 30 kd protein and 75 μg of the 90 kd protein were obtained.

The proteins were concentrated by acetone precipitation, and resuspended in 50 mM ammonium carbonate buffer, pH8. Tryptic digestion and HPLC purification were performed as described by Sturm and Chrispeels (*Jour. Biol. Chem.* (1987) 262:13392–13403). Briefly, digestion was performed by addition of trypsin (5% of sPs protein), and incubation for two hours at 37° C. The digestion was then repeated. The proteins were concentrated by lyophilization and resuspended in 50mM sodium phosphate buffer, pH2.2. This mixture was subjected to reverse phase HPLC separation by application to a C18 column in phosphate buffer. Elution was performed using an increasing gradient of acetonitrile. Eluted material from the phosphate buffer/acetonitrile gradient was monitored at 214 nm. The fractions corresponding to peaks of absorbance at 214 nm were collected, lyophilized, resuspended in 0.1% trifluoroacetic acid, reapplied to the C18 column (equilibrated with 0.1% trifluoroacetic acid), and eluted using an acetonitrile gradient. Eluted material from the trifluoroacetic acid/acetonitrile gradient was monitored at 214 nm. The fractions corresponding to peaks of absorbance at 214 nm were collected, lyophilized, and subjected to standard Edman degradation protein sequencing on an automated protein sequencer (Applied Biosystems; Foster City, Calif.). Sequences of 5 peptides were obtained. FIG. 3 (SEQ ID NOS: 1–5).

5. Isolation and Assembly of a Full-Length cDNA for SPS 5.1. RNA Isolation from Corn Leaf Total RNA was isolated from corn leaves (see 1.2.1.) according to the method of Turpen and Griffith (*Biotechniques* (1986) 4:11–15). Briefly, 250 gm of material was homogenized in 4M guanidine thiocyanate and 2% sarcosyl. The mixture was then centrifuged and the cleared supernatant was layered upon a 5.7M CsCl cushion and centrifuged for 5.5 hours at 50,000 RPM. The RNA pellet was dissolved in water, extracted with phenol and chloroform, and precipitated with ethanol. The resulting pellet was resuspended in water. The final yield of the RNA isolation was quantitated by UV spectrophotometry.

5.2. Poly(A) RNA Isolation

A saturated suspension of cellulose powder/water was added to the RNA/water mixture, at 10% of the total volume, to remove residual polysaccharides. After centrifugation, the supernatant, containing the RNA, was applied to an oligo (dT)-cellulose column as described by Maniatis et al. (*Molecular Cloning: A Laboratory Manual*, (1982) Cold Spring Harbor, N.Y.). The fraction containing the poly(A)+ RNA was then reapplied to the column. The eluted fraction containing the poly(A)+RNA was extracted with phenol, and the RNA was precipitated with ethanol. Analysis by gel electrophoresis showed complete absence of ribosomal RNA.

5.3. Construction of Total Corn Leaf Library cDNA synthesis was performed according to manufacturer's instructions (RiboClone cDNA Synthesis System by Promega, Madison, Wis.), using five μg of poly(A)+RNA as template, except that M-MLV reverse transcriptase (BRL; Bethesda, Md.) was substituted for AMV reverse transcriptase. EcoRI linkers were added to the blunt-ended cDNA, and the resulting fragments were cloned into an expression vector (LambdaZAP, Stratagene; La Jolla, Calif.) according to manufacturer's instructions. The resulting library contained approximately $1.5 \times 10^6$ transformants.

5.4. PCR Generation of a Partial SPS cDNA Probe

Using the sequence information from the peptides of Example 4 (SEQ ID NOS: 7–8) and the polymerase chain reaction (PCR), a 1200 bp SPS cDNA fragment was generated. Total corn leaf cDNA (5.3.) was used as a template, and degenerate oligonucleotides (SEQ ID NOS: 9–12), designed from two peptide sequences of the 30 kd and 90 kd SPS polypeptides, were used as primers. These primer sets were designated as CD3 (SEQ ID NOS: 9–10) and CD4. (SEQ ID NOS: 11–12) FIG. 4. PCR was carried out, according to manufacturer's instructions (GeneAmp DNA Amplification Reagent Kit and DNA Thermal Cycler of Perkin Elmer Cetus; Norwalk, Conn.) except that the reaction was carried out for 30 cycles, and the annealing steps were programmed to be 50° C. for 1 minute. The PCR reactions were analyzed by agarose gel electrophoresis. Use of the correct set of primers, which was CD3, resulted in a 1200 bp band being generated by the PCR reaction. PCR using the other set of primers, CD4, gave no specific signals. FIG. 5A and FIG. 5B. Southern analysis confirmed that the PCR band was not an artifact, as shown in FIG. 5A and FIG. 5B. The probe 4K5 (SEQ ID NO: 13) was used in that the corresponding sequence of the probe was predicted to be within the 1200 bp fragment if the fragment corresponded to the SPS sequence. The probe hybridized to the 1200 bp band generated by PCR using the primer set CD3 but not to PCR products generated by the primer set CD4 FIG. 5.

5.5 Isolation of SPS Bacteriophage Lambda cDNA Clones

The 1200 bp PCR-generated fragment was labeled with $^{32}P$ (as per the Random Primed DNA Labeling Kit, Boehringer Mannheim, Indianapolis, Ind.) and used as a probe to screen approximately 250,000 plaques of the cDNA library (5.3.). The inserts of the positive clones were analyzed by restriction analysis with EcoRI, and the clones with the longest inserts, SPS#3 and SPS#18, were selected for further analysis. FIG. 6. A 0.4 kb HindIII/EcoRI fragment from the 5' end of SPS#3 was isolated, then labeled with $^{32}P$ by random priming (Random Primed DNA Labeling Kit) and used as a probe to re-screen the library. Another clone, designated SPS#61, which extends further upstream than SPS#3, was isolated. FIG. 6. DNA sequencing indicated that the 5' end of the SPS reading frame was not reached.

To isolate cDNA clones that included more of the 5' region than SPS#3 or SPS#61, a new cDNA library was prepared, as per Example 5.3., (RiboClone cDNA Synthesis System by Promega; Madison, Wis.) using M-MLV reverse transcriptase instead of AMV reverse transcriptase. However, instead of using oligo (dT) as a primer, a synthetic 17 bp primer, 23B, derived from the 5' sequence of the SPS#61 clone, was used (FIG. 6). This resulted in cDNAs that only contain regions upstream of the the SPS#61 5' region. The library was screened with the $^{32}P$-labeled EcoRI insert from SPS#61, and 16 positive clones were obtained. The clones with the longest inserts, SPS#77 and SPS#90, were selected for further analysis. DNA sequencing of SPS#77 and SPS#90 showed that the region of overlap (greater than 100 bp) with SPS#61 was identical in all clones, and that both extend further upstream into the 5' region. FIG. 6

PCR was carried out using single-stranded cDNA (from a reverse transcriptase reaction corn leaf RNA (5.2.) primed with oligo (dT) T) as described above) as template and primers selected from the SPS#90 and SPS#3 sequences, confirmed that SPS#90 and SPS#3 originate from the same mRNA transcript. The fragment resulting from this PCR reaction was 750 bp in length, consistent with the the size predicted from the DNA sequence. The 750 bp fragment was subcloned into a Bluescript-derived vector as a SalI/HindIII fragment. Four of the resulting subclones were partially sequenced, and the sequence obtained matched the existing DNA sequence.

5.6. Assembly of the SPS Reading Frame.

Both DNA strands of #90, #61, and #3 were sequenced, using the method of Sanger et al. (PNAS (1977) 74: 5463–5467). All three sequences can be combined to one contiguous sequence of 3509 bp, (SEQ ID NO: 6) FIG. 7A through FIG. 7J. Primer extension experiments using corn leaf poly(A) RNA and an antisense primer showed that the 5' end of our DNA sequence represents sequences form the actual 5' end of the SPS in RNA. In the SPS reading frame, as defined by the five peptide sequences A8, B4, B11, 4R and 12N (SEQ ID NOS. 1–5), respectively, (FIG. 3), the first methionine codons are located at bp 112 and bp 250. FIG. 7. The codon at bp 112 is similar to the consensus eukaryotic translational start site (Kozak, Cell (1986) 44: 283–292) and is located 54 bp downstream of a TAG stop codon (bp 58). It is proposed that this codon represents the translational start of the SPS polypeptide in vivo. After a 1068 codon reading frame, translation is stopped by TGA. The following 193 bp contain the 3' untranslated region including a poly(A) addition signal, AAATAAA.

The full-length SPS coding region may be assembled by combining the 529 bp BamHI/HindIII fragment of SPS#90, the 705 bp HindIII fragment of SPS#61 and the 2162 bp HindIII/EcoRI fragment from SPS#3 (see FIG. 6).

6. Detection of SPS Polypeptides by Specific Antisera

Samples of purified protein preparations obtained by the method described in 3.2.2. were subjected to SDS-PAGE electrophoresis. The proteins in the gel were fixed and stained. The bands corresponding to the 90 kd and 30 kd polypeptides were excised. With this material polyclonal antisera were raised in rabbits by conventional procedures. Western analysis (as described by Oberfelder, Focus (1989) 11(1):1–5) showed that the antibodies isolated from the rabbit immunized with SPS 30 recognized the bands corresponding to the SPS 30 and SPS 120 peptides on a SDS PAGE gel, and that the antibodies isolated from the rabbit immunized with SPS 90 recognized the bands corresponding to the SPS 90 and SPS 120 polypeptides FIG. 8.

6.2. Immunological Localization of SPS in the Corn Plant

Total proteins were extracted from leaves of a 30 day-old corn plant, harvested at 11: 00 AM, by boiling in SDS buffer. The protein extracts were loaded on duplicate SDS-PAGE gels. One gel was stained with Coomassie Blue, while the other was subjected to Western analysis, using a mixture of SPS30 and SPS90 antisera as probe. FIG. 9A and FIG. 9B. The prominent bands appearing on the Coomassie Blue-stained gel were identified as phosphoenolpyruvate carboxylase (PEPcase), an enzyme involved in C4 photosynthesis. The Western blot showed the presence of the SPS band. The SPS protein pattern was very similar to the PEPcase protein pattern: not present in roots, and not present in the section of leaf closest to the the stem, or in very young leaves. This pattern corresponds with expression associated with photosynthesis, and is the pattern expected for SPS.

7. Construction of Expression Constructs Plasmids 7.1. Construction of the full-length SPS reading frame Clone SPS#90 is digested with HindIII and ligated with the 705 bp HindIII fragment from clone SPS#61 to create a plasmid containing the 5' end of the SPS coding region. The resulting plasmid is digested with BamHI and partially digested with HindIII, resulting in a 1340 bp BamHI/HindIII fragment containing the 5' end of the coding region. The 3' end of the SPS coding region is obtained by digestion of SPS#3 with EcoRI and partial digestion with HindIII, resulting in a 2162 bp HindIII/EcoRI fragment. This 2162 bp HindIII/EcoRI fragment, carrying the 3' end, is ligated with the 1340 BamHI/EcoRI fragment carrying the 5' end into a BamHI/EcoRI-digested pUC-derivative plasmid Bluescript, to create a plasmid carrying the entire 3403 bp SPS coding region and 3' untranslated transcription termination region.

7.2 Expression of SPS in E. coli

When cloning the 3403 bp BamHI/EcoRI SPS fragment into the plasmid Bluescript SK (Stratagene, La Jolla, Calif.), a translational fusion between the plasmid coded lacZ sequence and the SPS reading frame is created. The resulting fusion protein contains 30 N-terminal amino acids from the betagalactosidase and the complete SPS polypeptide. The fusion protein was expressed in E. coli under the Bluescribe plasmid lacZ promoter. Preparation of total protein followed by Western analysis using anti SPS antisera (6.1.) shows a band comigrating with native plant SPS. For SPS activity test the E. coli cells containing the SPS expression construct as described were opened with Lysozyme and sonication. Soluble protein was desalted by a Sephadex G-25 column. This protein extract was assayed for SPS activity analogous to (1.1.a.) except the reagent anthrone was used instead of resovcinol (E. U. Handel, Analytical Biochemistry, (1968) 22:280–283). This test shows that the SPS protein, expressed from the cDNA in E. coli does have SPS enzyme activity. By comparison to native plant enzyme it seems to have the same specific activity.

7.3. Construction of the Tobacco Small Subunit (SSU) Promoter-Transcriptional Fusions The SPS coding region can be conveniently cloned as a BamHI/EcoRI (bp 106–bp 3506) fragment 3' of a tobacco small subunit promoter.

A SSU promoter for expression of the SPS coding region, may be prepared as follows. The SSU promoter region from PCGN627(described below) is opened by KpnI and the 3' overhang removed. After EcoRI digestion, the 3403 bp BamHI (filled in) EcoRI SPS cDNA fragment (see, Example 7.1.) can be inserted.

After the SPS coding region is ligated into the SSU promoter, the SSU/SPS region may be ligated into a binary vector and integrated into a plant genome via Agrobacterium tumefaciens mediated transformation (The SPS region carries its own transcription termination region in the cDNA sequence.) Insertion of the ssu/SPS construct into the binary vector pCGN1557 results in pCGN3812.

pCGN627

The 3.4 kb EcoRI fragment of TSSU3-8 (O'Neal et al., *Nucleic Acids Res.* (1987) 15:9661-8677), containing the small subunit promoter region, is cloned into the EcoRI site of M13mp18 (Yanisch-Perron et al, *Gene* (1985) 53:103–119) to yield an M13 clone 8B. Single-stranded DNA is used as a template to extend oligonucleotide primer "Probe 1" (O'Neal et al., *Nucleic Acids Research* (1987) 15:8661-8677) using the Klenow fragment of DNA polymerase I. Extension products are treated with mung bean nuclease and then digested with HindIII to yield a 1450 bp fragment containing the SSU promoter region. The fragment is cloned into HindIII-SmaI-digested pUC18 (Yanisch-Perron et al., *Gene* (1985) 53: 103–119) to yield pCGN625. pCGN625 is digested with HindIII, the ends blunted with
  Klenow, and the digested plasmid re-digested with EcoRI.
  The =coRI/blunted-HindIII fragment containing the SSU promoter region is ligated with SmaI/EcoRI-digested pUC18 to yield pCGN627.

7.4. Construction of a CaMV Promoter - SPS Transcriptional Fusion

The 35S promoter DNA fragment from cauliflower mosaic virus can be fused to the SPS DNA as follows.

The plasmid pCGN639 can be opened by BamHI and EcoRI and the 3403 bp BamHI/EcoRI SPS cDNA fragment as described in Example 7.1 can be cloned into this plasmid. The hybrid gene can be removed from this plasmid as a 4.35 kb XbaI EcoRI fragment and ligated into a binary vector (K. E. McBride and K. R. Summerfelt, *Plant Mol. Bio.* (1990) 14:269–276) and integrated into a plant genome via *Agrobacterium tumefaciens* mediated transformation. Insertion of the CaMV/SPS construct into the binary vector pCGN1557 (McBride and Summerfelt supra) results in pCGN3815.

7.4.1. Construction of pCGN639 pCGN164 is digested with EcoRV and BamHI to release a EcoRV-BamHI fragment which contained a portion of the 35S promoter (bp 7340–7433). pCGN638 is digested with HindIII and EcoRV to release a HindIII-EcoRV fragment containing a different portion of the 35S promoter (bp 6493–7340). These two fragments are ligated into pCGN986 which has been digested with HindIII and BamHI to remove the HindIII-Bam/HI fragment containing the 35S-promoter; this ligation produces pCGN639, which contains the backbone and tml-3' region from pCGN986 and the two 35S promoter fragments from pCGN164 and pCGN638.

7.4.2. Construction of pCGN164

The AluI fragment of CaMV (bp 7144–7735) (Gardner et al., *Nucl.Acids Res.* (1981) 9:2871–2888) is obtained by digestion with AluI and cloned into the HindII site of M13mp7 (Vieira and Messing, *Gene* (1982) 19:259–268) to create c614. An coRI digest of C614 produces the EcoRI fragment from C614 containing the 35S promoter which is cloned into the EcoRI site of pUC8 (Vieira and Messing, supra) to produce pCGN146. To trim the promoter region, the BglII site (bp 7670) is treated with BglII and Bal31 and subsequently a BglII linker is attached to the Bal31 treated DNA to produce pCGN147. pCGN147 is digested with EcoRI/HphI and the resulting EcoRI-HphI fragment containing the 35S promoter is ligated into EcoRI-SmaI digested M13mp8 (Vieira and Messing, supra) to create pCGN164.

7.4.3. Construction of pCGN638

Digestion of CaMV10 (Gardner, et al., *Nucl. Acids Res.* (1981) 9:2871–2888) with BglII produces a BglII fragment containing a 35S promoter region (bp 6493–7670) which is ligated into the BamHI site of pUC19. (Norrander et al., *Gene* (1983) 26:101–106) to create pCGN638.

7.4.4. Construction of pCGN986 pCGN986 contains a cauliflower mosaic virus 35S (CaMV35) promoter and a T-DNA tml-3' region with multiple restriction sites between them. pCGN986 is derived from another cassette, pCGN206, containing a CaMV35S promoter and a different 3' region, the CaMV region VI 3'-end and pCGN971E, a tml 3' region.

pCGN148a containing a promoter region, selectable marker (kanamycin with 2 ATG's) and 3' region, is prepared by digesting pCGN528 with BglII and inserting the BamHI-BglII promoter fragment from pCGN147 (see above). This fragment is cloned into the BglII site of pCGN528 so that the BglII site is proximal to the kanamycin gene of pCGN528.

The shuttle vector used for this construct pCGN528, is made as follows: pCGN525 was made by digesting a plasmid containing TnS, which harbors a kanamycin gene (Jorgensen et al., *Mol. Gen. Genet.* (1979) 177:65), with HindIII-BamHI and inserting the HindIII-BamHI fragment containing the kanamycin resistance gene into the HindIII-BamHI sites in the tetracycline gene of pACYC184 (Chang and Cohen, *J. Bacteriol.* (1978) 134:1141–1156). pCGN526 was made by inserting the BamHI fragment 19 of pTiA6 (Thomashow et al., *Cell* (1980) 19:729–739) modified with XhoI linkers inserted into the SmaI site, into the DamHi site of pCGN525. pCGN528 was obtained by deleting the small XhoI and religating.

pCGN149a is made by cloning the BamHI kanamycin gene fragment from pMB9KanXXI into the BamHI site of pCGN148a. pMB9KanXXI is a pUC4K variant (Vieira and Messing, *Gene* (1982) 19:259–268) which has the XhoI site missing but contains a function kanamycin gene from Tn903 to allow for efficient selection in *Agrobacterium*.

pCGN149a is digested with HindIII and BamHi and ligated which pUC8 (Vieira and Messing, supra) digested with HindIII and BamHI to produce pCGN169. This removes the Tn903 kanamycin marker. pCGN565 and pCGN169 are both digested with HindIII and PstI and ligated to form pCGN203, a plasmid containing the CaMV 35S promoter and part of the 5'-end of the Tn5 kanamycin gene (up to the PstI site, (Jorgensen et al., *Mol. Gen. Genet.* (1979) 177:65). pCGN565 is a cloning vector based on pUC8-cm (K. Buckley, Ph.D. Thesis, UC San Diego 1985), but containing the polylinker from pUC18 (Yanisch-Perron et al., *Gene* (1985) 53:103–119).

A 3' regulatory region is added to pCGN203 from pCGN204 (an EcoRI fragment of CaMV (bp 408–6105) containing the region VI 3' cloned into pUC18 (Gardner et al., *Nucl. Acids Res.* (1981) 9:2871–2888) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., *Cell* (1980) 19:729–739) as a BamHI-EcoRI fragment (nucleotides 9062 to 12, 823, numbering as in (Barker et al., *Plant Mo. Biol.* (1983) 2:335–350) and combined with the pACYC184 (Chang and Cohen, *J. Bacteriol.* (1978) 134:1141–1156) origin of replication as an EcoRI-HindII fragment and a gentamycin resistance marker (from plasmid pLB41), (D. Figurski) as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers to yield pCGN971E. The resulting EcoRI-SacI fragment of pCGN971E, containing the tml 3' regulatory sequence is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligating with SalI linkers. The final expression cassette pCGN986 contains the CaMV 35S promoter followed by two SalI sites, an XbaI site, BamHI, SmaI, KpnI and the tml 3' region (nucleotides 11207-9023 of the T-DNA).

Here under are indication schemes of the constructs.

TABLE I

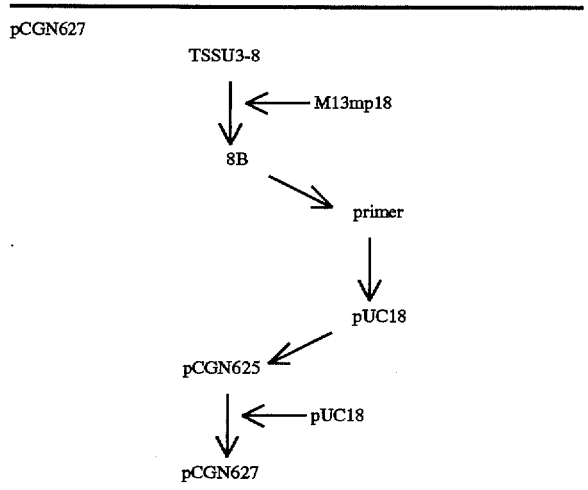

TABLE II

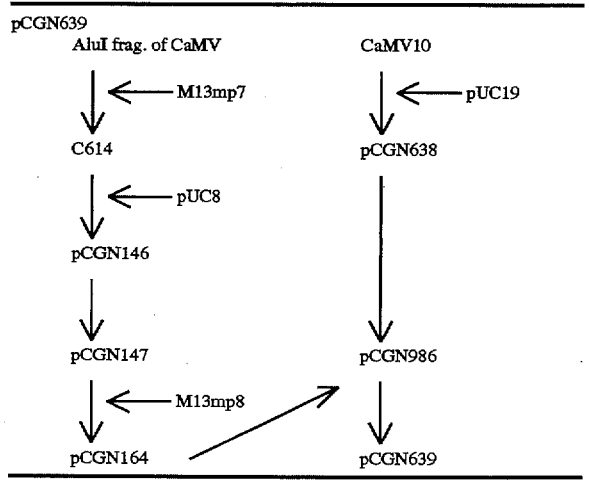

TABLE III

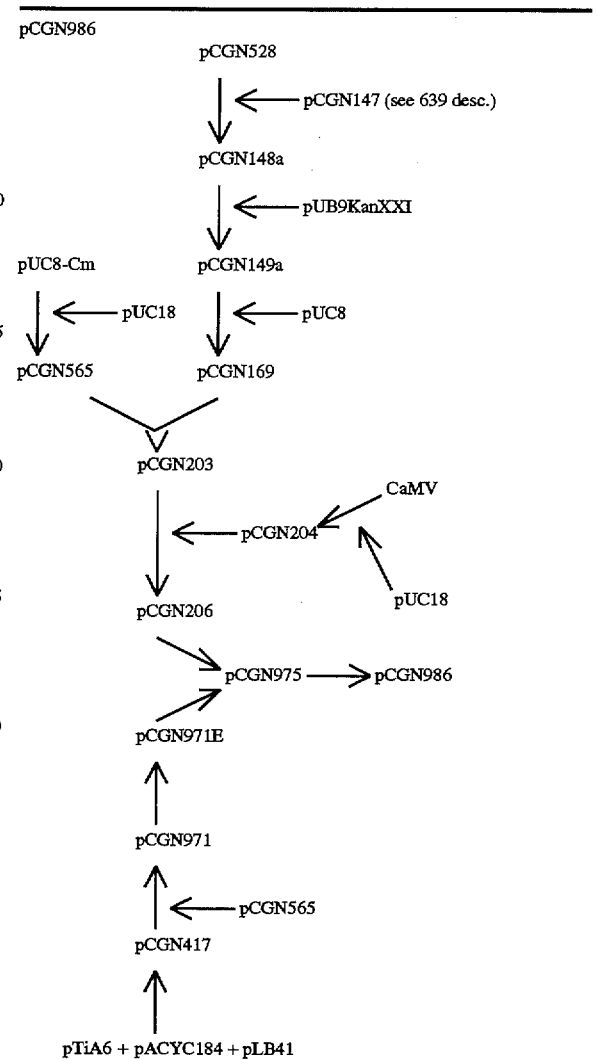

8. Transgenic SPS Tomato Plants

8.1 Production of SPS "Sense" Transgenic Tomato Plants

Tomato plants are transformed and regenerated with expression cassettes containing SPS encoding sequences (pCGN3812 and pCGN3815) via *Agrobacterium tumefaciens* mediated transformation (Fillatti, et al., *Bio/Technology* (1987) 5:726–730). Preparation of pCGN3812, a tobacco SSU/SPS construct, and pCGN3815, a CaMV 35S/SPS construct are described in Examples 7.3 and 7.4, respectively.

8.2 Immunoblot Results

Leaves from transformed tomato plants (pCGN3812 and pCGN3815) and control tomato and corn leaves may be tested as described in Example 6.2 for SPS activity using the SPS30 and SPS90 peptide polyclonal antisera of Example 6. No cross reactivity between the antisera and the control (endogenous) tomato is seen. This indicates that the corn and tomato SPS are not highly related. As to the transgenic tomato plants, leaf extracts from plants containing the pCGN3815 or pCGN3818 constructs show signals up to levels several times that observed by the untransformed corn leaf extracts.

8.3 SPS Activity

Leaf extracts are also tested for SPS activity according to the resorcinol protocol described in Example 1.1(a). In comparison of leaf extracts from control plants and transformed tomato plants containing the SPS gene, up to 12-fold increases are observed. Higher SPS activity is also observed in some leaf extracts from transgenic tomato plants containing the corn SPS gene as compared to control corn leaf extracts.

8.4 Starch & Sucrose Levels

Leaf tissue is analyzed for starch and sucrose levels according to the method of (Haissig, B. E., et al., *Physiol. Plan.* (1979) 47:151–157). Two controls are used, leaves from a first untransformed plant and leaves from a transformant which does not show any corn SPS immunoblot signal. The starch/sucrose levels of these two plants are essentially the same, having almost equal percentage of starch (mg/100 mg dry weight) and sucrose (mg/10 mg dry weight). High expressing plants containing pCGN3812 (pCGN3812-9 and pCGN3812-11) show both a reduction in leaf starch by 50% and an increase in sucrose levels by a factor of two. These data indicate that the presence of high levels of corn SPS in tomato leaves causes a modification of carbohydrate partitioning in this tissue.

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 1:

Thr Trp Ile Lys
 1

( 2 ) INFORMATION FOR SEQ ID NO: 2:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 2:

Tyr Val Val Glu Leu Ala Arg
 1               5

( 2 ) INFORMATION FOR SEQ ID NO: 3:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 3:

Ser Met Pro Pro Ile Trp Ala Glu Val Met Arg
 1               5                   1 0

( 2 ) INFORMATION FOR SEQ ID NO: 4:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 4:

Leu Arg Pro Asp Gln Asp Tyr Leu Met His Ile Ser His Arg 5,665,892

( 2 ) INFORMATION FOR SEQ ID NO: 5:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 5:

```
Trp  Ser  His  Asp  Gly  Ala  Arg
 1                    5
```

( 2 ) INFORMATION FOR SEQ ID NO: 6:

( i ) SEQUENCE CHARACTERISTICS:
        ( A ) LENGTH: 3509 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 6:

```
GAATTCCGGC GTGGGCGCTG GGCTAGTGCT CCCGCAGCGA GCGATCTGAG AGAACGGTAG    60

AGTTCCGGCC GGGCGCGCGG GAGAGGAGGA GGGTCGGGCG GGGAGGATCC G ATG GCC   117
                                                         Met Ala
                                                          1

GGG AAC GAG TGG ATC AAT GGG TAC CTG GAG GCG ATC CTC GAC AGC CAC   165
Gly Asn Glu Trp Ile Asn Gly Tyr Leu Glu Ala Ile Leu Asp Ser His
 5               10                  15

ACC TCG TCG CGG GGT GCC GGC GGC GGC GGC GGG GGG GAC CCC AGG       213
Thr Ser Ser Arg Gly Ala Gly Gly Gly Gly Gly Gly Asp Pro Arg
     20              25                  30

TCG CCG ACG AAG GCG GCG AGC CCC CGC GGC GCG CAC ATG AAC TTC AAC   261
Ser Pro Thr Lys Ala Ala Ser Pro Arg Gly Ala His Met Asn Phe Asn
 35              40                  45                  50

CCC TCG CAC TAC TTC GTC GAG GAG GTG GTC AAG GGC GTC GAC GAG AGC   309
Pro Ser His Tyr Phe Val Glu Glu Val Val Lys Gly Val Asp Glu Ser
 55              60                  65

GAC CTC CAC CGG ACG TGG ATC AAG GTC GTC GCC ACC CGC AAC GCC CGC   357
Asp Leu His Arg Thr Trp Ile Lys Val Val Ala Thr Arg Asn Ala Arg
     70                  75                  80

GAG CGC AGC ACC AGG CTC GAG AAC ATG TGC TGG CGG ATC TGG CAC CTC   405
Glu Arg Ser Thr Arg Leu Glu Asn Met Cys Trp Arg Ile Trp His Leu
 85                  90                  95

GCG CGC AAG AAG AAG CAG CTG GAG CTG GAG GGC ATC CAG AGA ATC TCG   453
Ala Arg Lys Lys Lys Gln Leu Glu Leu Glu Gly Ile Gln Arg Ile Ser
     100                 105                 110

GCA AGA AGG AAG GAA CAG GAG CAG GTG CGT CGT GAG GCG ACG GAG GAC   501
Ala Arg Arg Lys Glu Gln Glu Gln Val Arg Arg Glu Ala Thr Glu Asp
 115                 120                 125                 130

CTG GCC GAG GAT CTG TCA GAA GGC GAG AAG GGA GAC ACC ATC GGC GAG   549
Leu Ala Glu Asp Leu Ser Glu Gly Glu Lys Gly Asp Thr Ile Gly Glu
 135                 140                 145

CTT GCG CCG GTT GAG ACG ACC AAG AAG AAG TTC CAG AGG AAC TTC TCT   597
Leu Ala Pro Val Glu Thr Thr Lys Lys Lys Phe Gln Arg Asn Phe Ser
 150                 155                 160

GAC CTT ACC GTC TGG TCT GAC GAC AAT AAG GAG AAG AAG CTT TAC ATT   645
Asp Leu Thr Val Trp Ser Asp Asp Asn Lys Glu Lys Lys Leu Tyr Ile
 165                 170                 175
```

| | | | | | | | | | | | | | | | | |
|---|---|---|---|---|---|---|---|---|---|---|---|---|---|---|---|---|
| GTG | CTC | ATC | AGC | GTG | CAT | GGT | CTT | GTT | CGT | GGA | GAA | AAC | ATG | GAA | CTA | 693 |
| Val | Leu | Ile | Ser | Val | His | Gly | Leu | Val | Arg | Gly | Glu | Asn | Met | Glu | Leu | |
| | 180 | | | | 185 | | | | | 190 | | | | | | |
| GGT | CGT | GAT | TCT | GAT | ACA | GGT | GGC | CAG | GTG | AAA | TAT | GTG | GTC | GAA | CTT | 741 |
| Gly | Arg | Asp | Ser | Asp | Thr | Gly | Gly | Gln | Val | Lys | Tyr | Val | Val | Glu | Leu | |
| 195 | | | | | 200 | | | | | 205 | | | | | 210 | |
| GCA | AGA | GCG | ATG | TCA | ATG | ATG | CCT | GGA | GTG | TAC | AGG | GTG | GAC | CTC | TTC | 789 |
| Ala | Arg | Ala | Met | Ser | Met | Met | Pro | Gly | Val | Tyr | Arg | Val | Asp | Leu | Phe | |
| 215 | | | | | 220 | | | | | 225 | | | | | | |
| ACT | CGT | CAA | GTG | TCA | TCT | CCT | GAC | GTG | GAC | TGG | AGC | TAC | GGT | GAG | CCA | 837 |
| Thr | Arg | Gln | Val | Ser | Ser | Pro | Asp | Val | Asp | Trp | Ser | Tyr | Gly | Glu | Pro | |
| | 230 | | | | 235 | | | | | 240 | | | | | | |
| ACC | GAG | ATG | TTA | TGC | GCC | GGT | TCC | AAT | GAT | GGA | GAG | GGG | ATG | GGT | GAG | 885 |
| Thr | Glu | Met | Leu | Cys | Ala | Gly | Ser | Asn | Asp | Gly | Glu | Gly | Met | Gly | Glu | |
| 245 | | | | | 250 | | | | | 255 | | | | | | |
| AGT | GGC | GGA | GCC | TAC | ATT | GTG | CGC | ATA | CCG | TGT | GGG | CCG | CGG | GAT | AAA | 933 |
| Ser | Gly | Gly | Ala | Tyr | Ile | Val | Arg | Ile | Pro | Cys | Gly | Pro | Arg | Asp | Lys | |
| | 260 | | | | 265 | | | | | 270 | | | | | | |
| TAC | CTC | AAG | AAG | GAA | GCG | TTG | TGG | CCT | TAC | CTC | CAA | GAG | TTT | GTC | GAT | 981 |
| Tyr | Leu | Lys | Lys | Glu | Ala | Leu | Trp | Pro | Tyr | Leu | Gln | Glu | Phe | Val | Asp | |
| 275 | | | | | 280 | | | | | 285 | | | | | 290 | |
| GGA | GCC | CTT | GCG | CAT | ATC | CTG | AAC | ATG | TCC | AAG | GCT | CTG | GGA | GAG | CAG | 1029 |
| Gly | Ala | Leu | Ala | His | Ile | Leu | Asn | Met | Ser | Lys | Ala | Leu | Gly | Glu | Gln | |
| 295 | | | | | 300 | | | | | 305 | | | | | | |
| GTT | GGA | AAT | GGG | AGG | CCA | GTA | CTG | CCT | TAC | GTG | ATA | CAT | GGG | CAC | TAT | 1077 |
| Val | Gly | Asn | Gly | Arg | Pro | Val | Leu | Pro | Tyr | Val | Ile | His | Gly | His | Tyr | |
| | 310 | | | | 315 | | | | | 320 | | | | | | |
| GCC | GAT | GCT | GGA | GAT | GTT | GCT | GCT | CTC | CTT | TCT | GGT | GCG | CTG | AAT | GTG | 1125 |
| Ala | Asp | Ala | Gly | Asp | Val | Ala | Ala | Leu | Leu | Ser | Gly | Ala | Leu | Asn | Val | |
| 325 | | | | | 330 | | | | | 335 | | | | | | |
| CCA | ATG | GTG | CTC | ACT | GGC | CAC | TCA | CTT | GGG | AGG | AAC | AAG | CTG | GAA | CAA | 1173 |
| Pro | Met | Val | Leu | Thr | Gly | His | Ser | Leu | Gly | Arg | Asn | Lys | Leu | Glu | Gln | |
| | 340 | | | | 345 | | | | | 350 | | | | | | |
| CTG | CTG | AAG | CAA | GGG | CGC | ATG | TCC | AAG | GAG | GAG | ATC | GAT | TCG | ACA | TAC | 1221 |
| Leu | Leu | Lys | Gln | Gly | Arg | Met | Ser | Lys | Glu | Glu | Ile | Asp | Ser | Thr | Tyr | |
| 355 | | | | | 360 | | | | | 365 | | | | | 370 | |
| AAG | ATC | ATG | AGG | CGT | ATC | GAG | GGT | GAG | GAG | CTG | GCC | CTG | GAT | GCG | TCA | 1269 |
| Lys | Ile | Met | Arg | Arg | Ile | Glu | Gly | Glu | Glu | Leu | Ala | Leu | Asp | Ala | Ser | |
| 375 | | | | | 380 | | | | | 385 | | | | | | |
| GAG | CTT | GTA | ATC | ACG | AGC | ACA | AGG | CAG | GAG | ATT | GAT | GAG | CAG | TGG | GGA | 1317 |
| Glu | Leu | Val | Ile | Thr | Ser | Thr | Arg | Gln | Glu | Ile | Asp | Glu | Gln | Trp | Gly | |
| | 390 | | | | 395 | | | | | 400 | | | | | | |
| TTG | TAC | GAT | GGA | TTT | GAT | GTC | AAG | CTT | GAG | AAA | GTG | CTG | AGG | GCA | CGG | 1365 |
| Leu | Tyr | Asp | Gly | Phe | Asp | Val | Lys | Leu | Glu | Lys | Val | Leu | Arg | Ala | Arg | |
| 405 | | | | | 410 | | | | | 415 | | | | | | |
| GCG | AGG | CGC | GGG | GTT | AGC | TGC | CAT | GGT | CGT | TAC | ATG | CCT | AGG | ATG | GTG | 1413 |
| Ala | Arg | Arg | Gly | Val | Ser | Cys | His | Gly | Arg | Tyr | Met | Pro | Arg | Met | Val | |
| | 420 | | | | 425 | | | | | 430 | | | | | | |
| GTG | ATT | CCT | CCG | GGA | ATG | GAT | TTC | AGC | AAT | GTT | GTA | GTT | CAT | GAA | GAC | 1461 |
| Val | Ile | Pro | Pro | Gly | Met | Asp | Phe | Ser | Asn | Val | Val | Val | His | Glu | Asp | |
| 435 | | | | | 440 | | | | | 445 | | | | | 450 | |
| ATT | GAT | GGG | GAT | GGT | GAC | GTC | AAA | GAT | GAT | ATC | GTT | GGT | TTG | GAG | GGT | 1509 |
| Ile | Asp | Gly | Asp | Gly | Asp | Val | Lys | Asp | Asp | Ile | Val | Gly | Leu | Glu | Gly | |
| 455 | | | | | 460 | | | | | 465 | | | | | | |
| GCC | TCA | CCC | AAG | TCA | ATG | CCC | CCA | ATT | TGG | GCC | GAA | GTG | ATG | CGG | TTC | 1557 |
| Ala | Ser | Pro | Lys | Ser | Met | Pro | Pro | Ile | Trp | Ala | Glu | Val | Met | Arg | Phe | |
| | 470 | | | | 475 | | | | | 480 | | | | | | |
| CTG | ACC | AAC | CCT | CAC | AAG | CCG | ATG | ATC | CTG | GCG | TTA | TCA | AGA | CCA | GAC | 1605 |
| Leu | Thr | Asn | Pro | His | Lys | Pro | Met | Ile | Leu | Ala | Leu | Ser | Arg | Pro | Asp | |
| 485 | | | | | 490 | | | | | 495 | | | | | | |

```
CCG AAG AAG AAC ATC ACT ACC CTC GTC AAA GCG TTT GGA GAG TGT CGT    1653
Pro Lys Lys Asn Ile Thr Thr Leu Val Lys Ala Phe Gly Glu Cys Arg
    500             505             510

CCA CTC AGG GAA CTT GCA AAC CTT ACT CTG ATC ATG GGT AAC AGA GAT    1701
Pro Leu Arg Glu Leu Ala Asn Leu Thr Leu Ile Met Gly Asn Arg Asp
515             520             525             530

GAC ATC GAC GAC ATG TCT GCT GGC AAT GCC AGT GTC CTC ACC ACA GTT    1749
Asp Ile Asp Asp Met Ser Ala Gly Asn Ala Ser Val Leu Thr Thr Val
535             540             545

CTG AAG CTG ATT GAC AAG TAT GAT CTG TAC GGA AGC GTG GCG TTC CCT    1797
Leu Lys Leu Ile Asp Lys Tyr Asp Leu Tyr Gly Ser Val Ala Phe Pro
    550             555             560

AAG CAT CAC AAT CAG GCT GAC GTC CCG GAG ATC TAT CGC CTC GCG GCC    1845
Lys His His Asn Gln Ala Asp Val Pro Glu Ile Tyr Arg Leu Ala Ala
565             570             575

AAA ATG AAG GGC GTC TTC ATC AAC CCT GCT CTC GTT GAG CCG TTT GGT    1893
Lys Met Lys Gly Val Phe Ile Asn Pro Ala Leu Val Glu Pro Phe Gly
    580             585             590

CTC ACC CTG ATC GAG GCT GCG GCA CAC GGA CTC CCG ATA GTC GCT ACC    1941
Leu Thr Leu Ile Glu Ala Ala Ala His Gly Leu Pro Ile Val Ala Thr
595             600             605             610

AAG AAT GGT GGT CCG GTC GAC ATT ACA AAT GCA TTA AAC AAC GGA CTG    1989
Lys Asn Gly Gly Pro Val Asp Ile Thr Asn Ala Leu Asn Asn Gly Leu
615             620             625

CTC GTT GAC CCA CAC GAC CAG AAC GCC ATC GCT GAT GCA CTG CTG AAG    2037
Leu Val Asp Pro His Asp Gln Asn Ala Ile Ala Asp Ala Leu Leu Lys
    630             635             640

CTT GTG GCA GAC AAG AAC CTG TGG CAG GAA TGC CGG AGA AAC GGG CTG    2085
Leu Val Ala Asp Lys Asn Leu Trp Gln Glu Cys Arg Arg Asn Gly Leu
645             650             655

CGC AAC ATC CAC CTC TAC TCA TGG CCG GAG CAC TGC CGC ACT TAC CTC    2133
Arg Asn Ile His Leu Tyr Ser Trp Pro Glu His Cys Arg Thr Tyr Leu
    660             665             670

ACC AGG GTG GCC GGG TGC CGG TTA AGG AAC CCG AGG TGG CTG AAG GAC    2181
Thr Arg Val Ala Gly Cys Arg Leu Arg Asn Pro Arg Trp Leu Lys Asp
675             680             685             690

ACA CCA GCA GAT GCC GGA GCC GAT GAG GAG GAG TTC CTG GAG GAT TCC    2229
Thr Pro Ala Asp Ala Gly Ala Asp Glu Glu Glu Phe Leu Glu Asp Ser
695             700             705

ATG GAC GCT CAG GAC CTG TCA CTC CGT CTG TCC ATC GAC GGT GAG AAG    2277
Met Asp Ala Gln Asp Leu Ser Leu Arg Leu Ser Ile Asp Gly Glu Lys
    710             715             720

AGC TCG CTG AAC ACT AAC GAT CCA CTG TGG TTC GAC CCC CAG GAT CAA    2325
Ser Ser Leu Asn Thr Asn Asp Pro Leu Trp Phe Asp Pro Gln Asp Gln
725             730             735

GTG CAG AAG ATC ATG AAC AAC ATC AAG CAG TCG TCA GCG CTT CCT CCG    2373
Val Gln Lys Ile Met Asn Asn Ile Lys Gln Ser Ser Ala Leu Pro Pro
    740             745             750

TCC ATG TCC TCA GTC GCA GCC GAG GGC ACA GGC AGC ACC ATG AAC AAA    2421
Ser Met Ser Ser Val Ala Ala Glu Gly Thr Gly Ser Thr Met Asn Lys
755             760             765             770

TAC CCA CTC CTG CGC CGG CGC CGG CGC TTG TTC GTC ATA GCT GTG GAC    2469
Tyr Pro Leu Leu Arg Arg Arg Arg Leu Phe Val Ile Ala Val Asp
775             780             785

TGC TAC CAG GAC GAT GGC CGT GCT AGC AAG AAG ATG CTG CAG GTG ATC    2517
Cys Tyr Gln Asp Asp Gly Arg Ala Ser Lys Lys Met Leu Gln Val Ile
    790             795             800

CAG GAA GTT TTC AGA GCA GTC CGA TCG GAC TCC CAG ATG TTC AAG ATC    2565
Gln Glu Val Phe Arg Ala Val Arg Ser Asp Ser Gln Met Phe Lys Ile
805             810             815
```

| | | | | | | | | | | | | | | | | |
|---|---|---|---|---|---|---|---|---|---|---|---|---|---|---|---|---|
| TCA | GGG | TTC | ACG | CTG | TCG | ACT | GCC | ATG | CCG | TTG | TCC | GAG | ACA | CTC | CAG | 2613 |
| Ser | Gly 820 | Phe | Thr | Leu | Ser | Thr 825 | Ala | Met | Pro | Leu | Ser 830 | Glu | Thr | Leu | Gln | |
| CTT | CTG | CAG | CTC | GGC | AAG | ATC | CCA | GCG | ACC | GAC | TTC | GAC | GCC | CTC | ATC | 2661 |
| Leu 835 | Leu | Gln | Leu | Gly | Lys 840 | Ile | Pro | Ala | Thr | Asp 845 | Phe | Asp | Ala | Leu | Ile 850 | |
| TGT | GGC | AGC | GGC | AGC | GAG | GTG | TAC | TAT | CCT | GGC | ACG | GCG | AAC | TGC | ATG | 2709 |
| Cys 855 | Gly | Ser | Gly | Ser | Glu 860 | Val | Tyr | Tyr | Pro | Gly 865 | Thr | Ala | Asn | Cys | Met | |
| GAC | GCT | GAA | GGA | AAG | CTG | CGC | CCA | GAT | CAG | GAC | TAT | CTG | ATG | CAC | ATC | 2757 |
| Asp | Ala 870 | Glu | Gly | Lys | Leu | Arg 875 | Pro | Asp | Gln | Asp | Tyr 880 | Leu | Met | His | Ile | |
| AGC | CAC | CGC | TGG | TCC | CAT | GAC | GGC | GCG | AGG | CAG | ACC | ATA | GCG | AAG | CTC | 2805 |
| Ser 885 | His | Arg | Trp | Ser | His 890 | Asp | Gly | Ala | Arg | Gln 895 | Thr | Ile | Ala | Lys | Leu | |
| ATG | GGC | GCT | CAG | GAC | GGT | TCA | GGC | GAC | GCT | GTC | GAG | CAG | GAC | GTG | GCG | 2853 |
| Met | Gly 900 | Ala | Gln | Asp | Gly | Ser 905 | Gly | Asp | Ala | Val | Glu 910 | Gln | Asp | Val | Ala | |
| TCC | AGT | AAT | GCA | CAC | TGT | GTC | GCG | TTC | CTC | ATC | AAA | GAC | CCC | CAA | AAG | 2901 |
| Ser 915 | Ser | Asn | Ala | His | Cys 920 | Val | Ala | Phe | Leu | Ile 925 | Lys | Asp | Pro | Gln | Lys 930 | |
| GTG | AAA | ACG | GTC | GAT | GAG | ATG | AGG | GAG | CGG | CTG | AGG | ATG | CGT | GGT | CTC | 2949 |
| Val | Lys | Thr | Val | Asp 935 | Glu | Met | Arg | Glu | Arg 940 | Leu | Arg | Met | Arg | Gly 945 | Leu | |
| CGC | TGC | CAC | ATC | ATG | TAC | TGC | AGG | AAC | TCG | ACA | AGG | CTT | CAG | GTT | GTC | 2997 |
| Arg | Cys 950 | His | Ile | Met | Tyr | Cys 955 | Arg | Asn | Ser | Thr | Arg 960 | Leu | Gln | Val | Val | |
| CCT | CTG | CTA | GCA | TCA | AGG | TCA | CAG | GCA | CTC | AGG | TAT | CTT | TCC | GTG | CGC | 3045 |
| Pro 965 | Leu | Leu | Ala | Ser | Arg 970 | Ser | Gln | Ala | Leu | Arg 975 | Tyr | Leu | Ser | Val | Arg | |
| TGG | GGC | GTA | TCT | GTG | GGG | AAC | ATG | TAT | CTG | ATC | ACC | GGG | GAA | CAT | GGC | 3093 |
| Trp | Gly 980 | Val | Ser | Val | Gly | Asn 985 | Met | Tyr | Leu | Ile | Thr 990 | Gly | Glu | His | Gly | |
| GAC | ACC | GAT | CTA | GAG | GAG | ATG | CTA | TCC | GGG | CTA | CAC | AAG | ACC | GTG | ATC | 3141 |
| Asp | Thr | Asp | Leu | Glu 1000 | Glu | Met | Leu | Ser | Gly 1005 | Leu | His | Lys | Thr | Val 1010 | Ile | |
| | | | | | | | | | | | | | | | | |
| | | | | | | | | | | | | | | | | |
| GTC | CGT | GGC | GTC | ACC | GAG | AAG | GGT | TCG | GAA | GCA | CTG | GTG | AGG | AGC | CCA | 3189 |
| Val 1015 | Arg | Gly | Val | Thr | Glu 1020 | Lys | Gly | Ser | Glu | Ala 1025 | Leu | Val | Arg | Ser | Pro | |
| GGA | AGC | TAC | AAG | AGG | GAC | GAT | GTC | GTC | CCG | TCT | GAG | ACC | CCC | TTG | GCT | 3237 |
| Gly | Ser | Tyr | Lys 1030 | Arg | Asp | Asp | Val | Val 1035 | Pro | Ser | Glu | Thr | Pro 1040 | Leu | Ala | |
| GCG | TAC | ACG | ACT | GGT | GAG | CTG | AAG | GCC | GAC | GAG | ATC | ATG | CGG | GCT | CTG | 3285 |
| Ala 1045 | Tyr | Thr | Thr | Gly | Glu 1050 | Leu | Lys | Ala | Asp | Glu 1055 | Ile | Met | Arg | Ala | Leu | |
| AAG | CAA | GTC | TCC | AAG | ACT | TCC | AGC | GGC | ATG | TGAATTTGAT | GCTTCTTTTA | | | | | 3335 |
| Lys | Gln | Val 1060 | Ser | Lys | Thr | Ser 1065 | Ser | Gly | Met | | | | | | | |

CATTTGTCC TTTTCTTCAC TGCTATATAA AATAAGTTGT GAACAGTACC GCGGGTGTGT 3395

ATATATATAT TGCAGTGACA AATAAAACAG GACACTGCTA ACTATACTGG TGAATATACG 3455

ACTGTCAAGA TTGTATGCTA AGTACTCCAT TTCTCAATGT ATCAATCGGA ATTC 3509

( 2 ) INFORMATION FOR SEQ ID NO: 7:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: other nucleic acid (A) DESCRIPTION: possible peptide encoding sequences (iii) HYPOTHETICAL: Y (xi) SEQUENCE DESCRIPTION: SEQ ID NO: 7:

WSNATGCCNC CNATHTGGGC NGARGTNATG MGN    33

(2) INFORMATION FOR SEQ ID NO: 8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: possible peptide encoding sequences (iii) HYPOTHETICAL: Y (xi) SEQUENCE DESCRIPTION: SEQ ID NO: 8:

YTNMGNCCNG AYCARGAYTA YYTNATGCAY ATHWSNCAYM GN    42

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide mixture (xi) SEQUENCE DESCRIPTION: SEQ ID NO: 9:

ATGCCNCCNA THTGGGCNGA    20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide mixture (xi) SEQUENCE DESCRIPTION: SEQ ID NO: 10:

TGCATNAGRT ARTCYTGRTC    20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide mixture (xi) SEQUENCE DESCRIPTION: SEQ ID NO: 11:

TCNGCCCADA TNGGNGGCAT    20

(2) INFORMATION FOR SEQ ID NO: 12:

(i) SEQUENCE CHARACTERISTICS:
        (A) LENGTH: 20 base pairs
        (B) TYPE: nucleic acid -continued

```
        ( C ) STRANDEDNESS: single
        ( D ) TOPOLOGY: linear ( i i ) MOLECULE TYPE: other nucleic acid
            ( A ) DESCRIPTION: synthetic oligonucleotide mixture ( x i ) SEQUENCE DESCRIPTION: SEQ ID NO: 12:

GAYCARGAYT  AYCTNATGCA          2 0

( 2 ) INFORMATION FOR SEQ ID NO: 13:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: synthetic oligonucleotide mixture ( x i ) SEQUENCE DESCRIPTION: SEQ ID NO: 13:

TGRTCNGGNC  KNAR         1 4
```

We claim:

1. An isolated DNA encoding a sucrose phosphate synthase (SPS) derived from corn.

2. The DNA of claim 1 comprising the SPS encoding region shown in FIG. 7.

3. The DNA of claim 1 comprising cDNA.

4. The DNA of claim 1 comprising genomic DNA.

5. The DNA of claim 1 as present in a recombinant construct, wherein said DNA encoding a sucrose phosphate synthase is operably linked to a second DNA which is not naturally linked to said DNA encoding a sucrose phosphate synthase.

6. A recombinant construct comprising, as operably linked components in the 5' to 3' direction of transcription, a transcription initiation region functional in a vegetal cell and a DNA encoding a sucrose phosphate synthase (SPS) derived from corn.

7. The construct of claim 6 wherein said DNA encoding an SPS encodes a biologically active SPS.

8. The construct of claim 7 wherein said DNA encoding an SPS is in a sense orientation as to said transcription initiation region.

9. The construct of claim 8 further comprising a translation initiation region operably linked 3' to said transcription initiation region and 5' to said DNA encoding an SPS, wherein said translation initiation region is functional in a vegetal cell, and a transcription termination region functional in said vegetal cell 3' to said DNA encoding an SPS.

10. The construct of claim 9 wherein said transcription termination region is an SPS gene transcription termination region.

11. The construct of claim 6 wherein said DNA encoding an SPS comprises the SPS encoding region shown in FIG. 7.

12. The construct of claim 6 wherein said transcription initiation region is tissue specific.

13. The construct of claim 12 wherein said transcription initiation region is leaf specific.

14. A method of modifying the starch and sucrose levels in a tomato vegetal cell, said method comprising:

growing a tomato vegetal cell having integrated into its genome a construct comprising, as operably linked components in the 5' to 3' direction of transcription, a transcription initiation region functional in said tomato vegetal cell and a DNA encoding a sucrose phosphate synthase derived from corn, wherein said DNA encoding said sucrose phosphate synthase derived from corn is not naturally linked to said transcription initiation region, wherein said tomato vegetal cell is grown under conditions which permit said transcription initiation region to function, and wherein growing said tomato vegetal cell under said conditions permits said DNA encoding said sucrose phosphate synthase derived from corn to be expressed at a level which modifies the starch and sucrose levels in said tomato vegetal cell from a given ratio of starch to sucrose, as measured in control plant cells, to a different ratio of starch to sucrose.

15. The method of claim 14 where said tomato vegetal cell is a leaf cell.

16. A tomato vegetal cell having integrated into its genome a recombinant construct of any one of claims 6–13, 60–61 and 64–65.

17. A tomato plant comprising cells having integrated into its genome a recombinant construct of any one of claims 6–13, 60–61 and 64–65.

18. A tomato vegetal cell having a modified ratio of starch to sucrose, wherein said cell is produced according to the method comprising growing a tomato vegetal cell having integrated into its genome a construct of any one of claims 6–13 under conditions which permit said transcription initiation region to function, and wherein growing said vegetal cell under said conditions permit said construct to be expressed at a level which modifies the starch and sucrose levels in said vegetal cell, whereby the ratio of starch to sucrose level in said tomato vegetal cell is modified as compared to a given ratio of starch to sucrose measured in control plant cells.

19. A plant produced from a tomato vegetal cell of claim 18.

20. The method of claim 14, wherein said DNA encoding a sucrose phosphate synthase derived from corn is in a sense orientation as to said transcription initiation region.

21. The method of claim 20 wherein said construct further comprises a translation initiation region functional in a tomato vegetal cell operably linked 3' to said transcription initiation region and 5' to said DNA encoding, said sucrose phosphate synthase derived from corn and a transcription termination region functional in said tomato vegetal cell operably linked 3' to said DNA encoding said sucrose phosphate synthase derived from corn.

22. The method of claim 14 wherein said transcription initiation region is tissue specific.

23. The method of claim 22 wherein said transcription initiation region is leaf specific.

24. A tomato vegetal cell having modified levels of starch and sucrose, wherein said modified levels of starch and sucrose are produced according to the method of claim 14.

25. A method of increasing the yield of a tomato plant comprising:

growing a plant, wherein the genome of said plant comprises an integrated chimeric DNA construct capable of providing for expression of sucrose phosphate synthase derived from corn at a level sufficient to increase the amount of sucrose in tomato fruit by a factor of about 2 and decrease the amount of leaf starch by about 50% as compared to the amount of sucrose and starch measured in a control tomato plant, whereby an increase in plant yield is obtained.

26. An isolated DNA encoding a sucrose phosphate synthase wherein said DNA comprises at least about 10 nucleotides up to the full length of nucleotides represented by SEQ ID NO: 6.

27. The DNA sequence according to claim 26, wherein said DNA sequence encodes an amino acid sequence represented by a SEQ ID NO selected from the group consisting of SEQ ID NO: 1, SEQ ID NO:2, SEQ ID NO:3, SEQ ID NO:4 and SEQ ID NO:5.

28. The DNA of claim 26 comprising cDNA.

29. The DNA of claim 26 comprising genomic DNA.

30. The isolated DNA encoding a sucrose phosphate synthase according to claim 26 as present in a recombinant construct, wherein said DNA encoding a sucrose phosphate synthase is operably linked to a second DNA which is not naturally linked to said DNA encoding a sucrose phosphate synthase.

31. A recombinant construct comprising, as operably linked components in the 5' to 3' direction of transcription, a transcription initiation region functional in a tomato vegetal cell and said DNA encoding a sucrose phosphate synthase according to claim 26.

32. The construct of claim 31 wherein said DNA encoding a sucrose phosphate synthase encodes a biologically active sucrose phosphate synthase.

33. The construct of claim 32 wherein said DNA encoding a sucrose phosphate synthase is in a sense orientation as to said transcription initiation region.

34. The construct of claim 33 further comprising a translation initiation region operably linked 3' to said transcription initiation region and 5' to said DNA encoding a sucrose phosphate synthase, wherein said translation initiation region is functional in a tomato vegetal cell, and a transcription termination region functional in said vegetal cell 3' to said DNA encoding an SPS.

35. The construct of claim 34 wherein said transcription termination region is a sucrose phosphate synthase gene transcription termination region.

36. The construct of claim 31 wherein said transcription initiation region is tissue specific.

37. The construct of claim 36 wherein said transcription initiation region is leaf specific.

38. A nucleic acid sequence encoding a peptide wherein said peptide has an amino acid sequence represented by a SEQ ID. NO: selected from the group consisting of SEQ ID. NO: 1, SEQ ID. NO: 2, SEQ ID. NO: 3, SEQ ID. NO: 4, and SEQ ID. NO: 5.

39. A tomato vegetal cell having integrated into its genome a recombinant construct according to claim 30.

40. A leaf cell having integrated into its genome a recombinant construct according to claim 30.

41. A tomato plant comprising cells according to claims 39 or 40.

42. A tomato vegetal cell having a modified ratio of starch to sucrose, wherein said cell is produced according to the method comprising growing a tomato vegetal cell having integrated into its genome a construct according to claim 30 under conditions which permit said transcription initiation region to function, and wherein growing said tomato vegetal cell under said conditions permit said construct to be expressed at a level which modifies the starch and sucrose levels in said tomato vegetal cell, whereby the ratio of starch to sucrose level in said tomato vegetal cell is modified as compared to a given ratio of starch to sucrose measured in control plant cells.

43. A tomato plant produced from a tomato vegetal cell of claim 42.

44. A method of increasing the yield of a tomato plant sink tissue, said method comprising:

growing a tomato plant having integrated into its genome a construct comprising, as operably linked components in the 5' to 3' direction of transcription, a transcription initiation region functional in a tomato plant cell and a DNA encoding a sucrose phosphate synthase derived from corn, wherein said DNA encoding a sucrose phosphate synthase is not naturally linked to said transcription initiation region, and wherein said tomato plant cell is grown under conditions which permit said transcription initiation region to function, whereby the amount of sucrose available to said tomato plant sink tissue is increased compared to the amount of sucrose measured in a control tomato plant sink tissue.

45. The method of claim 44 wherein said transcription initiation region is tissue specific.

46. The method of claim 45 wherein said transcription initiation region is functional in a fruit cell.

47. The method of claim 45 wherein said transcription initiation region is functional in a leaf cell.

48. The method of claim 47 wherein said transcription initiation region is a Rubisco small subunit promoter.

49. The method of claim 44, wherein increasing the amount of sucrose available in tomato plant sink tissue increases the amount of total solids per unit weight of said sink tissue compared to the amount of total solids per unit weight measured in a control tomato plant sink tissue.

50. The method of claim 44 wherein said sink tissue is fruit tissue.

51. The method of claim 49, wherein said weight is dry weight.

52. A method of increasing the amount of soluble solids in a tomato plant sink tissue, said method comprising:

growing a tomato plant having integrated into its genome a construct comprising, as operably linked components in the 5' to 3' direction of transcription, a transcription initiation region functional in a tomato plant cell and a DNA encoding a sucrose phosphate synthase derived from corn, wherein said DNA encoding a sucrose phosphate synthase is not naturally linked to said transcription initiation region, and wherein said tomato plant cell is grown under conditions which will permit said transcription initiation region to function, whereby the amount of soluble solids per unit weight of said tomato plant sink tissue is increased compared to the amount of solids measured in a control plant sink tissue; and whereby starch is converted to sucrose in said tomato plant cell and whereby an increased level of sucrose is made available to said tomato plant sink tissue.

53. The method of claim 52 wherein said transcription initiation region is tissue specific.

54. The method of claim 53 wherein said transcription initiation region is functional in a tomato fruit cell.

55. The method of claim 53 wherein said transcription initiation region is functional in a tomato leaf cell and wherein said sucrose is transported into said sink tissue.

56. The method of claim 55 wherein said transcription initiation region is a Rubisco small subunit promoter.

57. The method of claim 52 wherein said sink tissue is fruit tissue.

58. The method of claim 52 wherein the amount of sucrose in said tomato plant sink tissue is increased compared to the amount of sucrose measured a control tomato plant sink tissue.

59. The method of claim 52 wherein the amount of glucose and fructose in said sink tissue is increased compared to the amount of glucose and fructose measured in a control tomato plant sink tissue.

60. The construct of claim 6 wherein said transcription initiation region is a cauliflower mosaic virus 35S promoter region.

61. The construct of claim 13 wherein said transcription initiation region is a Rubisco small subunit promoter region.

62. The method of claim 14 wherein said transcription initiation region is a cauliflower mosaic virus 35S promoter region.

63. The method of claim 23 wherein said transcription initiation region is a Rubisco small subunit promoter region.

64. The construct of claim 31 wherein said transcription initiation region is a cauliflower mosaic virus 35S promoter region.

65. The construct of claim 37 wherein said transcription initiation region is a Rubisco small subunit promoter region.

66. The method of claim 44 wherein said transcription initiation region is a cauliflower mosaic virus 35S promoter region.

67. The method of claim 52 wherein said transcription initiation region is a cauliflower mosaic virus 35S promoter region.

* * * * *

UNITED STATES PATENT AND TRADEMARK OFFICE
CERTIFICATE OF CORRECTION

PATENT NO. : 5,665,892
DATED : September 9, 1997
INVENTOR(S) : Van Assche et al.

It is certified that error appears in the above-identified patent and that said Letters Patent is hereby corrected as shown below:

<u>Title page,</u>
Item [73], Assignee, should be -- Calgene, Inc., Davis, Calif. and Roussel UCLAF, Paris, France --

Signed and Sealed this

Twenty-second Day of July, 2003

JAMES E. ROGAN
*Director of the United States Patent and Trademark Office*